(12) United States Patent
Matousek et al.

(10) Patent No.: US 10,935,440 B2
(45) Date of Patent: Mar. 2, 2021

(54) CLINICAL THERMOMETER

(71) Applicant: United Kingdom Research and Innovation, Swindon (GB)

(72) Inventors: Pavel Matousek, Oxfordshire (GB); Nicholas Stone, Exeter (GB); Benjamin Gardner, Exeter (GB)

(73) Assignee: United Kingdom Research and Innovation, Swindon (GB)

( * ) Notice: Subject to any disclaimer, the term of this patent is extended or adjusted under 35 U.S.C. 154(b) by 131 days.

(21) Appl. No.: 15/740,217

(22) PCT Filed: Jun. 29, 2016

(86) PCT No.: PCT/GB2016/051951
§ 371 (c)(1),
(2) Date: Dec. 27, 2017

(87) PCT Pub. No.: WO2017/001847
PCT Pub. Date: Jan. 5, 2017

(65) Prior Publication Data
US 2018/0188117 A1    Jul. 5, 2018

(30) Foreign Application Priority Data

Jul. 1, 2015 (GB) .................................. 1511574
Sep. 25, 2015 (GB) .................................. 1516996

(51) Int. Cl.
*A61B 5/01* (2006.01)
*G01K 11/12* (2021.01)
(Continued)

(52) U.S. Cl.
CPC ............ *G01K 11/12* (2013.01); *G01K 13/002* (2013.01); *G01K 13/02* (2013.01); *A61B 5/01* (2013.01)

(58) Field of Classification Search
CPC .. G01K 11/32; G01K 13/02; G01K 2011/322; G01D 5/35364; G01J 3/44;
(Continued)

(56) References Cited

U.S. PATENT DOCUMENTS 5,046,854 A * 9/1991 Weller .................... G01N 21/03
                                                                      250/576
5,272,334 A    12/1993 Sai
(Continued)

FOREIGN PATENT DOCUMENTS

EP        0300529 A1    1/1989
WO      94/25861       11/1994
(Continued)

OTHER PUBLICATIONS

Abu-Absi et al., "Real Time Monitoring of Multiple Parameters in Mammalian Cell Culture Bioreactors Using an In-Line Raman Spectroscopy Probe," Biotechnology and Bioengineering, 2010, pp. 1-7.

(Continued)

*Primary Examiner* — Gail Kaplan Verbitsky
(74) *Attorney, Agent, or Firm* — Preti Flaherty; Beliveau & Pachios LLP

(57) ABSTRACT

The disclosure relates to a clinical thermometer for non-invasive measurement of sub-cutaneous temperature of tissue of a human or animal subject. Probe light is collected from a collection region spatially offset from an entry region on a visible surface of the subject, following scattering within the tissue, and a temperature of the tissue is determined from Raman spectral features in the collected light.

48 Claims, 14 Drawing Sheets

(51) Int. Cl.
*G01K 13/00* (2021.01)
*G01K 13/02* (2021.01)

(58) Field of Classification Search
CPC .......... G01J 3/4412; G01J 5/0896; G01J 3/10;
G01J 5/08; G01J 5/60; G01N 21/658;
G01N 21/65; A61B 5/0075; A61B 5/01;
A61B 5/1455; A61B 5/00; A61B 5/1477
USPC ........ 374/120, 121, 130, 137, 141, 160, 161
See application file for complete search history.

(56) References Cited

U.S. PATENT DOCUMENTS

| | | | | |
|---|---|---|---|---|
| 5,553,616 | A | * | 9/1996 | Ham ................. A61B 5/14558 600/316 |
| 6,070,093 | A | * | 5/2000 | Oosta ................. A61B 5/0095 356/39 |
| 6,377,828 | B1 | * | 4/2002 | Chaiken ............. A61B 5/14532 356/301 |
| 6,567,678 | B1 | * | 5/2003 | Oosta ................. A61B 5/0095 356/364 |
| 6,868,285 | B2 | * | 3/2005 | Muller-Dethlefs ......................... A61B 5/14532 600/316 |
| 6,992,759 | B2 | * | 1/2006 | Nakayama ......... G01N 21/0303 250/339.07 |
| 7,413,341 | B1 | | 8/2008 | Kachynski et al. |
| 7,475,724 | B2 | | 1/2009 | Pribnow et al. |
| 8,243,269 | B2 | * | 8/2012 | Matousek ............ A61B 5/0059 356/301 |
| 8,902,425 | B2 | * | 12/2014 | Babic ................. G01B 9/02055 356/364 |
| 9,778,172 | B2 | * | 10/2017 | Pelletier .................... G01J 3/10 |
| 2003/0174384 | A1 | | 9/2003 | Halas et al. |
| 2005/0117150 | A1 | | 6/2005 | Puppels et al. |
| 2007/0027373 | A1 | * | 2/2007 | Xie .................... A61B 5/14532 600/316 |
| 2007/0282182 | A1 | * | 12/2007 | Messerges ........... A61B 5/0059 600/324 |
| 2008/0076985 | A1 | | 3/2008 | Matousek et al. |
| 2008/0204742 | A1 | | 8/2008 | Halas et al. |
| 2008/0246947 | A1 | * | 10/2008 | Lees ...................... G01K 11/32 356/51 |
| 2009/0022204 | A1 | | 1/2009 | Kurth et al. |
| 2010/0011769 | A1 | * | 1/2010 | Gambacorta ........ F23M 20/005 60/725 |
| 2010/0049007 | A1 | * | 2/2010 | Sterling ............. A61B 5/14552 600/301 |
| 2010/0145200 | A1 | | 6/2010 | Mahadevan-Jansen et al. |
| 2011/0213216 | A1 | * | 9/2011 | McKenna ............. A61B 5/0002 600/301 |
| 2015/0164336 | A1 | * | 6/2015 | Mahadevan-Jansen ...................... A61B 5/0091 600/477 |
| 2015/0247755 | A1 | * | 9/2015 | Pelletier .................. G01J 5/522 356/440 |
| 2015/0313533 | A1 | * | 11/2015 | Rapp ...................... A61B 5/447 600/476 |
| 2016/0157757 | A1 | * | 6/2016 | Murthy ................ A61B 5/4839 600/310 |
| 2017/0003226 | A1 | * | 1/2017 | Parker .................... G01N 21/65 |
| 2018/0042583 | A1 | * | 2/2018 | Pringle ................ A61B 1/2736 |
| 2018/0045570 | A1 | * | 2/2018 | Smith ...................... G01J 3/06 |
| 2018/0372540 | A1 | * | 12/2018 | Zhao ...................... G01N 21/65 |

FOREIGN PATENT DOCUMENTS

| | | |
|---|---|---|
| WO | 2003/073082 A1 | 9/2003 |
| WO | 2006/061565 A1 | 6/2006 |
| WO | 2006/061566 A1 | 6/2006 |
| WO | 2007/113566 A2 | 10/2007 |
| WO | 2010/018557 A1 | 2/2010 |
| WO | WO2011065970 A * | 6/2011 |
| WO | 2014/149071 A1 | 9/2014 |

OTHER PUBLICATIONS

Bagavathiappan et al., "Infrared thermography for condition monitoring—A review," Infrared Physics & Technology 60, 2013, pp. 35-55.
Buckley et al., "Non-invasive analysis of turbid samples using deep Raman spectroscopy," Analyst, 2011, pp. 3039-3050.
Huang et al., "Plasmonic photo-thermal therapy (PPTT)," Alexandria Journal of Medicine, 2011, vol. 47, pp. 1-9.
Hynynen et al., "Temperature Monitoring in Fat with MRI," Magnetic Resonance in Medicine, 2000, vol. 43, pp. 901-904.
Lahiri et al., "Medical applications of infrared thermography: A review," Infrared Physics & Technology, 2012, vol. 55, pp. 221-235.
Levick et al., "Validation of microwave radiometry for measuring the internal temperature profile of human tissue," Measurement Science and Technology, 2011, vol. 22, pp. 1-8.
Maher et al., "Temperature-Dependent Anti-Stokes/Stokes Ratios under Surface-Enhanced Raman Scattering Conditions," J. Phys. Chem, 2006, vol. 110, pp. 6797-6803.
Matousek et al., "Numerical Simulations of Subsurface Probing in Diffusely Scattering Media Using Spatially Offset Raman Spectroscopy," Applied Spectroscopy, 2005, vol. 59, No. 12, pp. 1485-1492.
Matousek et al., "Subsurface Probing in Diffusely Scattering Media Using Spatially Offset Raman Spectroscopy," Applied Spectroscopy, 2005, vol. 59, No. 4, pp. 393-400.
Matousek, "Inverse Spatially Offset Raman Spectroscopy for Deep Noninvasive Probing of Turbid Media," Applied Spectroscopy, 2006, vol. 60, No. 11, pp. 1341-1347.
Matousek et al., "Recent advances in the development of Raman spectroscopy for deep non-invasive medical diagnosis," J. Biophotonics, 2013, vol. 6, No. 1, pp. 7-19.
Pozzi et al., "Evaluating Single-Molecule Stokes and Anti-Stokes Sers for Nanoscale Thermometry," The Journal of Physical Chemistry, 2015, vol. 119, pp. 21116-21124.
Stone et al., "Surface enhanced spatially offset Raman spectroscopic (SESORS) imaging—the next dimension," Chemical Science, 2011, vol. 2, pp. 776-780.
Stone et al., "Prospects of Deep Raman Spectroscopy for Noninvasive Detection of Conjugated Surface Enhanced Resonance Raman Scattering Nanoparticles Buried within 25 mm of Mammalian Tissue," Analytical Chemistry, 2010, vol. 82, No. 10, pp. 3969-3973.
Vo-Dinh et al., "SERS Nanosensors and Nanoreporters: Golden Opportunities in Biomedical Applications," Advanced Review, 2015, vol. 7, pp. 17-33.
Search Report for Application No. GB1516996.4 dated Mar. 18, 2016.
International Search Report and Written Opinion for International Application No. PCT/GB2016/051951 dated Sep. 6, 2016.
Damaghi M. et al., "pH sensing and regulation in cancer," Frontiers in Physiology, No. 4, Art. 370 (2013).
Garg, R. et al., "Optical transmission in highly concentrated dispersions," Journal of the Optics Society of America A, vol. 15, pp. 932-935 (1998).
Hashim, A.I. et al., "Imaging pH and Metastasis," NMR Biomedical, vol. 24, No. 6, pp. 582-591 (2011).
Jaworska, A. et al., "SERG-based monitoring of the intracellular pH in endothelial cells: the influence of the extracellular environment and tumour necrosis factor-α," Analyst, vol. 140, pp. 2321-2329 (2015).
Matousek, P. and Parker, A.W., "Bulk Raman Analysis of Pharmaceutical Tablets," Applied Spectroscopy, vol. 60, pp. 1353-1357 (2006).
Rindelaub, J.D. et al., "Direct Measurement of pH in Individual Particles via Raman Microspectroscopy and Variation in Acidity with Relative Humidity," Journal of Physical Chemistry A, vol. 120, pp. 911-917 (2016).

(56) References Cited

OTHER PUBLICATIONS

Schrader, B. and Bergmann, G., "Die Intensitat des Ramanspektrums polykristalliner Substanzen," Zeitschrift fur Analystische Chemie Fresenius, pp. 230-247 (1967). English summary.

Vardaki, M.Z. et al., "Studying the distribution of deep Raman spectroscopy signals using liquid tissue phantoms with varying optical properties," Analyst, vol. 140, pp. 5112-5119 (2015).

Wang, F. et al., "Surface-Enhanced Raman Scattering Detection of pH with Silica-Encapsulated 4-Mercaptobenzoic Acid-Functionalized Silver Nanoparticles," Analytical Chemistry, vol. 84, pp. 8013-8019 (2012).

Williams, Adam et al., "Multivariate spectral analysis of pH SERS probes for improved sensing capabilities: Spectral analysis of pH SERS probes," Journal of Raman Spectroscopy, vol. 47, No. 7, pp. 819-827, Jul. 1, 2016.

International Search Report and the Written Opinion of the International Searching Authority, for related International Application PCT/GB2017/053241, dated Feb. 9, 2018.

Schrader, B. and Bergmann, G., "Die Intensitat des Ramanspektrums polykristalliner Substanzen," Zeitschrift fur Analystische Chemie Fresenius, pp. 230-247 (1967). English summary.

Vo-Dinh et al., "SERS Nanosensors and Nanoreporters: Golden Opportunities in Biomedical Applications," WIRES Nanomed Nanobiotechnol 2015, 7:17-33. doi: 10.1002/wman.1283.

Jaworska, A. et al., "SERS-based monitoring of the intracellular pH in endothelial cells: the influence of the extracellular environment and tumour necrosis factor-α," Analyst, vol. 140, pp. 2321-2329 (2015).

\* cited by examiner

CLINICAL THERMOMETER

The present invention relates to a clinical thermometer for non-invasive measurement of subcutaneous temperature, and to corresponding methods. More generally, the invention relates to methods and apparatus for measuring temperature of a sub-surface volume of a sample, for example where the sample is diffusely scattering.

INTRODUCTION

Thermometers for clinical use to measure human or animal body temperature traditionally operate on the basis of a liquid such as mercury or alcohol contained in a glass bulb and capillary tube, with thermal expansion of the liquid giving rise to an indication of the temperature. In recent years, electrical thermometers using a thermocouples or thermistors, and infrared thermometers have come into common use.

Thermometers based on liquid expansion and electrical thermometers are usually based on providing a good thermal contact between a part of the thermometer and the patient's body. Infrared thermometers rely on radiation emitted by a surface of the patient, for example the ear drum, inside the mouth, or some other area of the skin, and in the form of an infrared camera may be used to provide thermal imagery of a patient.

It is known to use microwave radiometry to provide non-invasive thermometry of internal body temperature. However, this technique relies on the natural thermal black-body radiation emitted by tissue in the lower microwave region, and the extremely low power levels of such radiation make such devices complex and expensive, while the centimetre wavelength range of the detected radiation limits the spatial resolution of such techniques.

It would be desirable to provide a clinical thermometer suitable for non-invasive subcutaneous use which addresses problems and limitations of the related prior art. It would also be desirable more generally to provide improved apparatus and methods for determining sub-surface temperature of samples.

SUMMARY OF THE INVENTION

The invention provides an optical clinical thermometer for subcutaneous temperature measurement, and optionally such a thermometer which can determine a temperature profile over depth beneath the sample surface.

More generally, the invention provides methods and apparatus for optical measurement of sub-surface temperature of a sample. The temperature may be derived for a plurality of depths or ranges of depth within a sample using techniques of spatially offset Raman spectroscopy, and may be determined without contact with the sample. In particular, the invention directs probe light to one or more first, entry regions on the sample surface, and collects the probe light, following scattering within the sample, from one or more second, collection regions some or all of which are separate from and/or spaced from and/or spatially offset from the one or more entry regions. The collected light then contains spectral features arising from Raman scattering within the sample which can be analysed to determine one or more temperatures at one or more depths or ranges of depth within the sample.

The temperature can be determined by noting that corresponding Stokes and anti Stokes Raman band intensities vary differently with temperature, and that such differences can therefore be used to measure temperature. Corresponding Stokes and anti Stokes spectral features include or comprise spectral lines, peaks or bands which arise, typically, from the same vibrational excitation of the same molecule, and are therefore symmetric in wavenumber distribution.

In particular, the invention provides a method of measuring temperature in a sub-surface volume of a sample, comprising: directing probe light to an entry region on the sample surface; collecting said probe light from a collection region on the sample surface, following scattering within the subsurface volume of the sample, the collection region being spatially offset from the entry region; detecting one or more Raman spectral features in the collected probe light; and determining a temperature of the subsurface volume from the one or more Raman spectral features.

Determining a temperature of the subsurface volume from the one or more Raman spectral features may comprise determining the temperature using differences between one or more Stokes features and the corresponding anti Stokes features in the detected Raman spectral features. Generally speaking, temperature may be determined from ratios of properties of corresponding Stokes and anti Stokes features, such as intensities, heights or powers in particular spectral lines. However, various different techniques can be used to analyse the spectral features, including statistical methods which are trained to determine temperature from regions of the Stokes and anti Stokes spectra.

It is also possible to determine temperature of the sub-surface volume from one or more Raman spectral features using only Stokes or only anti-Stokes features. For example, because the intensities of individual anti-Stokes bands vary non-linearly with temperature, the relative intensity of different (for example neighbouring) anti-Stokes bands can be used to determine temperature, or a surface temperature determined in another manner could be used to provide reference for intensities of one or more bands against which spectral features from sub-surface regions can be compared to determine sub-surface temperature. Alternatively, some Stokes or anti-Stokes Raman bands may be shifted in frequency, e.g. due to anharmonic coupling to low lying vibrational modes. The effect can also be utilised as a thermal probe.

Because Raman spectral features are specific to particular chemical species, embodiments of the invention can determine temperature of a particular chemical species or material within the sample, by analysing spectral features specific to that species. Some particular applications of this aspect of the invention include the monitoring of a chemical reaction where reactants are not in thermal equilibrium with their surroundings or in non-thermally equilibrated samples with thermal gradients between different chemical constituents.

The method may comprise separately detecting said one or more Raman spectral features in the collected probe light for each of a plurality of different spatial offsets between said entry and collection regions. Because the path of scattering through the sample volume is on average deeper for wider spatial offsets, this technique provides depth information and enables associating the Raman features from each of said plurality of different spatial offsets with a different depth or distribution of depth within the sample, therefore also enabling a determination of a separate temperature for each of one or more depths or distributions of depth within the sample.

The method may also comprise setting said entry and collection regions to be coincident or overlapping. In this case, the detected Raman spectral features are strongly biased in their origin towards the surface of the sample, typically approximately within or less than about 1 photon transport length of the surface (i.e. the distance over which the photon direction is just fully randomized). The Raman spectral features detected when the entry and collection regions are spatially offset may then be compensated for the unwanted (and often overwhelming) surface contribution using the Raman spectral features detected when the entry and collection regions are coincident or overlapping. Another use of this data is to determine a temperature of the sample surface from the one or more Raman spectral features detected when the entry and collection regions are coincident or overlapping, using differences between the Stokes/anti Stokes features in the collected light.

The entry and collection regions may be shaped, spaced, offset and otherwise arranged and moved in a variety of ways. However, in some embodiments the entry region comprises one or more segments which are located around a centrally disposed collection region, for example as an annulus disposed around the collection region. Such arrangements provide for a relatively large entry region reducing the risk of damage through heating or burning by the probe light.

Irrespective of particular shape and arrangement, the entry and collection regions may typically be spatially offset by an offset by a distance in the range from 1 mm to 50 mm, and more preferably in the range from 3 mm to 20 mm. The optimum or chosen offset or range of offsets will depend on the sample. Embodiments of the invention may also make use of a null or zero offset between the entry and collection regions, in which the regions are coincident or overlapping, for example to provide a signal representative of the surface of the sample which can be used for subtraction, calibration or other compensation of signals obtained at non zero offsets.

Typically, the sample may be a diffusely scattering sample, or the sub-surface volume for which temperature is determined may be diffusely scattering. In this case, the degree to which the sample or volume is diffusely scattering may be represented by photon transport length within the diffusely scattering region, which may typically be less than about 3 mm, say around 1 mm for human tissue, and in the region of around 0.1 to 1 mm for translucent plastics, pharmaceutical powders and tablets, body fluids such as blood and other turbid liquids or interest.

Although the entry and collection regions may be adjacent, proximal, or spaced apart on a surface which is largely planar or only moderately curved, thereby using a backscatter configuration, the entry and collection regions may also lie on parts of the surface with substantially different surface normal vectors, for example with normals in the region of 90 degrees apart, or even in the region of 180 degrees apart, and any angle or range in-between. For example, the entry and collection regions may be disposed on opposite or opposing sides of a sample, or such that a subsurface volume the temperature of which is being determined by the invention lies directly between the entry and collection regions. Such arrangements may be described as transmission configurations.

In such circumstances where the entry and collection regions are not substantially coplanar, a plurality of offsets between the entry and collection regions can still be used. For example, entry and collection regions may be arranged such that the local normals of the sample surface for the two regions takes on a range of different angle values, for example within the full range of 0 to 360 degrees around the sample.

Transmission arrangements in which material of the sample lies directly between the entry and collection regions may be of particular interest where the sample is small, for example being only of the order of about 5 mm to about 50 mm in diameter or thickness for strongly scattering samples, although larger diameters or spacings between entry and collection regions could be used for more transparent samples.

Methods of the invention maybe applied to a variety of circumstances, for example to determine temperature of a fluid within a containing wall, such as a fluid in a conduit or chamber. The entry and collection regions are then provided on said containing wall, for example on windows of the containing wall, and the subsurface volume comprises a volume of the fluid. The chamber could be a chamber of a bioreactor or other vessel.

The invention is applicable to determining a sub surface temperature of a subsurface region of tissue of a human or animal subject. The surface on which the entry and collection regions are located may then typically be a surface of the skin of the subject, and the subcutaneous temperature is then determined as a single value, or as a function of depth by using multiple spatial offsets. To this end, the invention also provides a method of non-invasive measurement of sub-cutaneous temperature of tissue of a human or animal subject, comprising: directing probe light to an entry region on a visible surface of the subject; collecting said probe light from a collection region on the visible surface, following scattering within the tissue, the collection region being spatially offset from the entry region; detecting Stokes and corresponding anti Stokes Raman spectral features in the collected probe light; and determining a temperature of the tissue from differences between the Stokes and anti Stokes Raman spectral features.

The invention also provides methods in which one or more Surface Enhanced Raman Spectroscopy (SERS) substrates are provided in the sub-surface volume of the sample such that the detected one or more Raman spectral features in the collected probe light comprise one or more SERS spectral features, such that temperature within the subsurface volume can be determined from the SERS spectral features. Typically, the SERS spectral features will be SERS spectral features of one or more particular chemical components adjacent to, bonded or coupled to, or otherwise proximal to the one or more SERS substrates. The determined temperature may then be considered representative of the chemical components and SERS substrate. The one or more SERS substrates may comprise one or more nanoparticles, nanospheres, nanoshells, nanorods, extended rough or patterned metal (or metalized) surfaces, or one or more substrates comprising SERS active surface features. Nanoparticles with a noble metal surface are commonly used.

If the sub-surface volume of the sample comprises human or animal tissue, the methods described herein may further comprising heating a sub-surface volume of the sample in various ways, such as by using plasmonic heating of the one or more SERS substrates or of one or more other substrates. Other techniques of heating which may be used include radio and magnetic heating. Such heating may be used for various thermal therapies in which elevated tissue temperatures are used to damage surrounding tissue, to activate or enhance the effect of drugs of other agents, and so forth, for example in order to damage, for example, tumour tissue or cancer cells. In such thermal therapy techniques, substrates to remotely effect the heating in the tissue may be disposed there by direct injection, through transport through the body in the lymph and blood systems, and in other ways.

Using subsurface measurement of temperature as described herein, whether detected using SERS particles or without, the described methods may further comprise controlling the step of heating the sub-surface tissue, or other subsurface volume of the sample, in response to the determined temperature of the sub-surface volume. This feedback control can be used to maintain the target volume at a desired temperature, or within a desired range, or to control the temperature to follow a desired profile in time.

The invention also provides apparatus corresponding to the above methods, for example a clinical thermometer for determining a temperature in tissue beneath a visible surface of a human or animal subject, comprising: a light source arranged to form a beam of probe light directed to an entry region on the visible surface; collection optics arranged to receive said probe light from a collection region on the surface following scattering within the tissue, the collection region being spaced from the entry region; a spectral analyser arranged to detect corresponding Stokes and anti Stokes Raman scattering spectral features in the probe light received through the collection optics; and a processor arranged to determine a temperature in the tissue from differences between the Stokes and anti Stokes Raman spectral features.

Such a clinical thermometer may conveniently be provided as an integral and/or handheld unit, for example including a power supply such as a battery, along with suitable control and data readout elements.

More generally, the invention provides apparatus for measuring temperature within a volume of a sample having a surface, comprising: a light source for generating probe light; delivery optics arranged to direct the probe light to an entry region on the surface; collection optics arranged to collect said probe light from a collection region on the surface, following scattering within the volume of the sample, the collection region being spatially offset from the entry region; a spectral analyser arranged to detect Raman spectral features in the collected probe light; and a processor arranged to determine a temperature of the volume from the Raman spectral features.

The processor may be arranged to determine a temperature of the subsurface volume from the Raman spectral features using differences between one or more Stokes features and corresponding anti Stokes features in the detected Raman spectral features, and may be arranged to determine a temperature of a particular chemical component present in the volume, by detecting Raman features characteristic of the particular chemical component, and by determining the temperature of the particular chemical component from the detected Raman features characteristic of the particular chemical component.

To enable multiple spatial offsets to be used, and therefore a depth profile of temperature to be derived, the apparatus may comprise an offset driver arranged to provide a plurality of different spatial offsets between said entry and collection regions, the apparatus being arranged to separately detect said Raman spectral features for each different spatial offset, and to associate the Raman features from each of said plurality of different spatial offsets with a different depth or distribution of depths within the sample. The processor is then arranged to combine said Raman features from said different spatial offsets to determine a separate temperature for each of one or more depths or distributions of depth within the sample. For example, a plurality of spatial offsets may be used in the range from 1 mm to 50 mm, and more preferably in the range from 3 mm to 20 mm, depending on the nature of the sample and the design of the apparatus.

Zero or null spatial offsets or spacings, and transmission configurations of the entry and collection regions may also be used as already discussed above.

The invention also provides apparatus comprising a fluid or other material within a containing wall, in combination with temperature determining apparatus as described herein arranged such the entry and collection regions are provided on said containing wall, and the subsurface volume comprises a volume of the fluid or other material, the apparatus being arranged to determine a temperature of the fluid or other material. The containing wall may at least partly defines a conduit within which a fluid, powder or other material is flowing, or the containing wall may be the wall of a chemical reactor vessel or bioreactor with the fluid comprising reagents within the vessel or bioreactor.

The invention also provides apparatus for carrying out thermal therapy on a human or animal subject by controlling the heating of a region of tissue responsive to a temperature of the region of tissue detected using the described SORS techniques, whether through Raman scattering using SERS substrates or without SERS substrates. To this end, the apparatus may comprise a heating driver arranged to control the heating of the region of tissue responsive to the determined temperature of the region of tissue. If SERS substrates are used for the Raman scattering for the purposes of temperature detection, the apparatus may also be arranged to provide the desired tissue heating using plasmonic heating of the same substrates, or of other substrates, which could be suitably selected or designed nanoparticles, typically having metal surfaces or being formed wholly of metal. Noble metals such as gold and silver are frequently used for these purposes. The plasmonic heating may be carried out for example using laser radiation.

The processor may typically be implemented using one or more microprocessors with associated memory storing program instructions for carrying out the analysis of detected Raman spectral features as described herein, for the determination of temperature. The processor may also be used for suitable control of one or more of the light source, and the offset driver for setting the spatial offset between entry and collection regions, and may be connected to a display for displaying operational information of the apparatus and an input device for receiving operating instructions. The apparatus may also be arranged to display the determined temperature or temperature profile, for example on the display, or to output such information using a network or other data connection.

BRIEF DESCRIPTION OF THE DRAWINGS

Embodiments of the invention will now be described, by way of example only, with reference to the accompanying drawings, of which:

FIG. 11 shows how the invention may be applied to a bioreactor or similar;

DETAILED DESCRIPTION OF EMBODIMENTS

Figure 1:
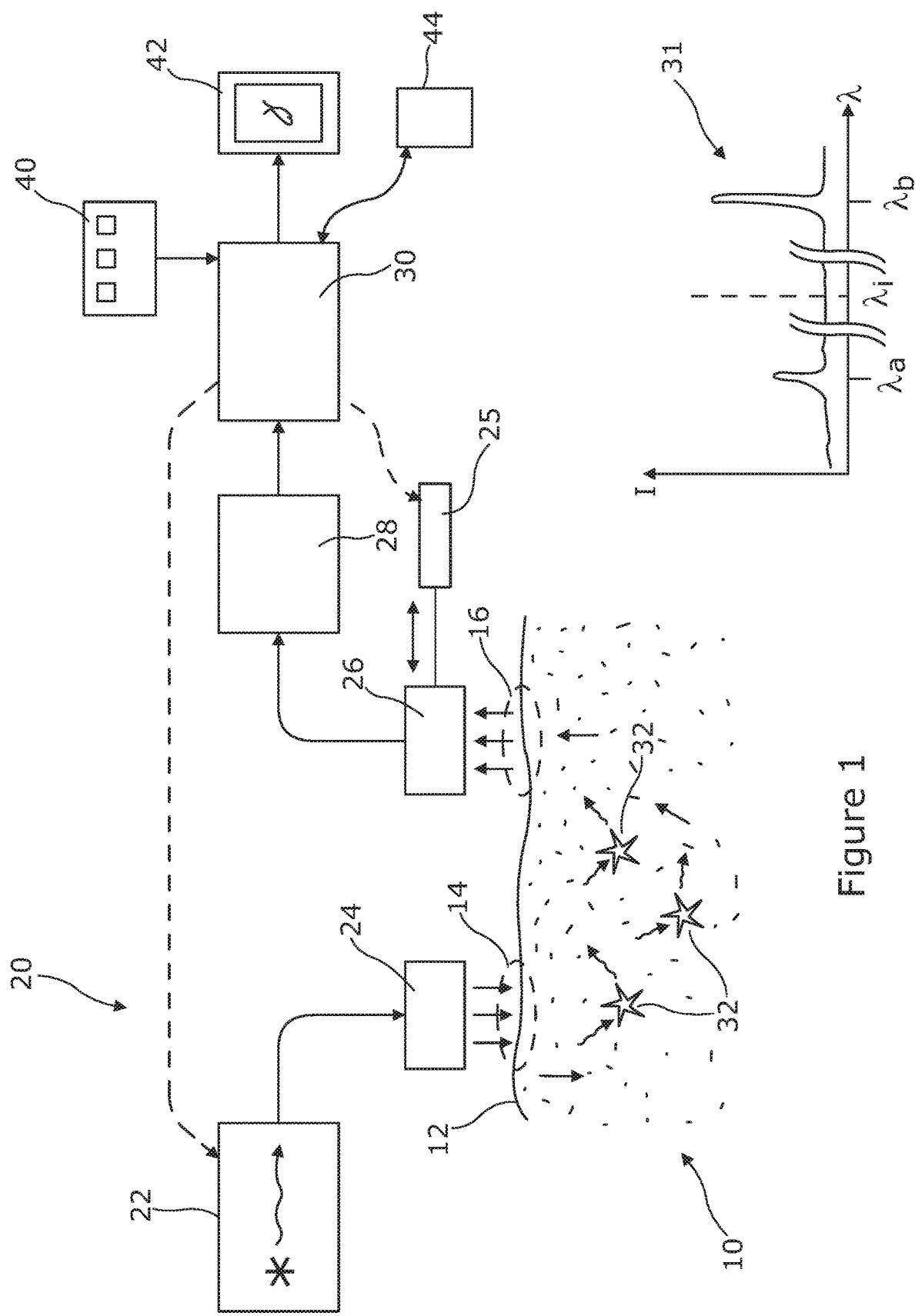
FIG. 1 schematically shows apparatus according to the invention for optically determining a temperature in a subsurface volume of a sample.

Referring now to FIG. 1 there is shown schematically apparatus 20 for measuring temperature in a sub-surface volume of a sample 10. The apparatus may be, for example, a thermometer for determining a temperature beneath a visible surface of patient, in which case the thermometer may be described as a clinical or medical thermometer, and may be used for non-invasive detection of a sub-cutaneous or other sub-surface temperature. In such cases the sample 10 is body tissue of a patient, and the surface 12 of the sample may be defined as a surface of the skin of the patient or some other exposed membrane such as the surface of the cornea. Various other applications for the invention in determining sub surface temperature of a sample are discussed elsewhere in this document.

The apparatus comprises a light source 22 arranged to form a beam of probe light, and delivery optics 24 arranged to direct the beam of probe light to an entry region 14 on the surface 12 of the sample 10. Collection optics 26 are arranged to collect probe light, which has been scattered within the sample 10, from a collection region 16 spatially offset from the entry region 14. Optional relative movement of the entry and collection regions, to provide a plurality of offsets, may be provided by an offset driver mechanism 25, which may form part of or be combined with or be arranged to control the delivery optics and/or the collection optics.

A spectral analyser 28 then receives the collected light, and detects spectral features in the collected light which relate to scattering of the probe light within the sample. Data relating to the detected spectral features are then used by a processor 30 to determine temperature of a sub-surface volume or region of the sample from the detected spectral features. Using the optional offset driver, the apparatus may be arranged to separately detect Raman spectral features for each of a plurality of different offsets between the entry and collection regions, so as to provide a more depth selective determination of temperature, and/or temperatures at multiple depths.

The light source 22 may typically be a near infrared laser, emitting a beam of probe light in the near infrared region of the electromagnetic spectrum, for example at a wavelength of around 800 nm. The delivery optics 24 may be provided by one or more suitable optical fibres and/or lenses arranged to form the beam of probe light into a suitably configured entry region 14 on the surface of the sample. The collection optics 26 may also be provided by one or more suitable optical fibres and/or lenses to define the collection region 16 on the surface of the sample and to collected probe light from this region and deliver it to the spectral analyser 28. The spectral analyser 28 may be provided in various ways such as using a spectrometer such as a dispersive spectrometer, or by suitable optical filters in combination with photodetectors, or in other ways, in order to detect particular spectral features in the collected light.

Aspects of the spectral features detected by the spectral analyser 28 are illustrated in FIG. 1 at graph 31. In this graph, the wavelength of the probe light generated by the light source 22 is depicted as $\lambda_i$. Typically, this wavelength of light may be suppressed or substantially removed by the collection optics 26, before the collected light is received by the spectral analyser 28, for example using a suitable optical filter, so that there is no corresponding central peak shown in the graph 31. In order to determine a temperature of a sub-surface volume of the sample from the detected spectral features, the detected spectral features include Raman spectral features resulting from Raman scattering within the sample 10. Such scattering is shown in FIG. 1 by reference numeral 32.

The Raman scattering spectral features include both Stokes features which result from loss of energy of a probe light photon during Raman scattering, and anti-Stokes features which result from gain of energy of a probe light photon during Raman scattering. The wavelength shift (often discussed in Raman spectroscopy in terms of wavenumber shift for independence from the probe light wavelength) from the wavelength of the photon before Raman scattering is dependent on the identity of the molecule from which the photon is scattered, with a particular chemical species giving rise to a particular spectrum of Raman scattering with spectral features which are symmetric in wavenumber between the Stokes and anti Stokes directions in terms of their positions. In FIG. 1 a Raman spectral feature arising from Stokes shift is depicted as peak $\lambda_s$, and a corresponding anti Stokes shift feature is depicted as peak $\lambda_a$.

Although corresponding Stokes and anti-Stokes features form a symmetric pattern around the probe light wavelength before scattering, the intensities of a Stokes feature and a corresponding anti Stokes feature are not the same. Instead, the anti Stokes feature is generally of much lower intensity, with the ratio of intensities of a Stokes feature and the corresponding anti-Stokes feature being temperature dependent due to the fact that the anti Stokes features are solely due to vibrationally excited molecules, whereas the Stokes features derive their intensities from molecules in the ground state as well as in vibrationally excited states. The intensity ratio can be approximated using the following formula:

$$\frac{I_{anti-Stokes}}{I_{Stokes}} = \mathrm{Exp}\left(\frac{-E}{kT}\right)$$

where k is the Boltzmann's constant, T is the temperature in Kelvin, and E is the first vibrational energy state.

The processor 30 therefore preferably determines temperature of a sub-surface volume of the sample 10 using detected properties, such as intensities or powers, of corresponding Stokes and anti-Stokes features in the detected Raman features. The temperature may be determined using a ratio of the intensities of a particular corresponding pair of Stokes and anti Stokes features using the equation above, or in other ways. For example, a detected Raman spectrum will typically contain a large number of Raman spectral features, and the determination of temperature may make use of a plurality of such features, for example taking ratios of particular pairs of features and averaging the ratios. More generally, mathematical techniques may be used by the processor 30 to derive relationships between the Stokes and anti-Stokes spectra and temperature, to derive a statistical relationship which may then subsequently be used by the apparatus to determine temperature during monitoring or operation. For example, a technique using a method of partial least squares to achieve this is described in more detail below.

Note that the processor may alternatively determine a temperature of a sub-surface region using detected properties of only anti-Stokes or only Stokes features. For example, because the intensities of individual anti-Stokes bands vary non-linearly with temperature, the relative intensity of different (for example neighbouring) anti-Stokes bands could be used to determine temperature. Alternatively or additionally a surface temperature determined in another manner in combination with spectral features from the sample surface could be used to provide reference intensities for one or more bands against which spectral features from sub-surface regions can be compared to determine sub-surface temperature.

The processor 30 may also be used to provide control and/or monitoring of other elements of the apparatus, for example of the light source 22 and the offset driver 25. An input 40 may be used to provide user input or control instructions to the apparatus by connection to the processor, and a display 42 may be used by the apparatus to output operational information. The determined temperature(s) or temperature profile(s) may also be presented to a user on the display 42, and/or output to another entity using a data connection 44. Of course, the input 40 and display 42 could be combined into a single touch screen display if desired.

If a single or multiple pairs of spectral features are to be used, these may be selected to result from one or more particular chemical species within the sample so that a determined temperature is indicative of a temperature of that chemical species, which in some circumstances may not be the same as a bulk temperature of the sample. Various situations in which this may be a relevant technique or consideration are where a substance or compound has been administered to a human or animal subject, and has become comprised in tissue of the subject, and the described techniques are used to determine the temperature of that particular substance of compound. Similarly, the described embodiments may be used for monitoring temperatures of a chemical reaction where one or more chemical constituents (such as a catalyst substrate and direct chemical reactants) are at different temperatures to each other due to endothermic or exothermic processes, or colocation or proximity to such endothermic or exothermic processes.

The proportion of scattering of the probe light within the sample which is inelastic Raman scattering, compared with the proportion of scattering which is elastic scattering is typically very small, usually with a difference of many orders of magnitude, and especially when the sample is highly scattering as is typically the case with human tissue. As a consequence, most photons of probe light are not Raman scattered. However, each photon of probe light which is Raman scattered within the sample is also subsequently scattered elastically a large number of times, giving rise to a random walk of the photon through the sample. The average path of this random walk through the subsurface volume of the sample, between the entry region and the collection region, depends on the spatial offset between these regions. It can be seen that for larger spatial offsets the average depth of the path will be deeper within the sample.

Using this principle, the spacing between the entry and collection regions can be controlled or adjusted by the apparatus 20 in order to control the distribution of depths at which the Raman scattering occurs. This technique is referred to as spatially offset Raman spectroscopy, and is discussed in detail in WO2006/061565 and WO2006/061566, the contents of which are incorporated herein by reference for all purposes, including for illustrating how characteristics of the sample may be determined at particular depths and profiles of depth within the sample. According to the present invention, such characteristics may include temperature of the sample, or temperature of one or more particular chemical components of the sample. Some ways in which Raman spectral features or related information from different spatial offsets may be combined to derive characteristics of the sample selected for one or more depths or one or more profiles of depths, are discussed in the above patent publications, but may include simple subtraction schemes for example in which the spectral features for a small or null offset are subtracted from those of one or more larger offsets, or more complex multivariate analysis, such as principle component analysis in which statistical relationships between detected spectral features at multiple offsets are used to derive temperature at a depth, profile of depth, or multiple such depths or profiles of depth. According to the principles of spatially offset Raman spectroscopy, therefore, the entry and collection regions may be of various sizes and shapes, and for any particular spatial offset these regions may each be formed by single contiguous or multiple discrete segments on the surface of the sample. Some examples of such regions are depicted in FIGS. 2a and 2b.

Figure 2A:
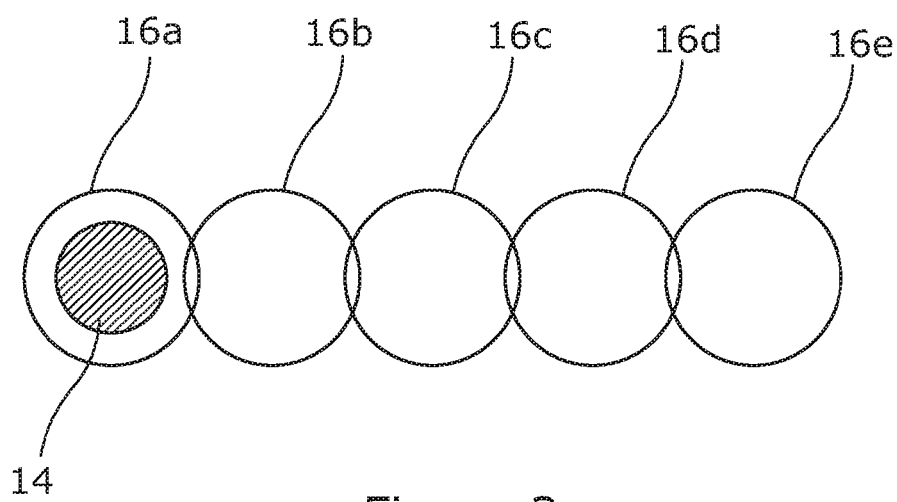
FIGS. 2a and 2b show some configurations for spaced probe light entry and collection regions into the sample.

In FIG. 2a, an entry region 14 is provided at a fixed position, and multiple collection regions 16a-16d are provided at increasing spatial offsets from the single entry region. Optionally, one of the illustrated collection regions 16a is coincident with, or overlapping with the entry region 14, so as to form a zero offset or null spacing. This zero offset can conveniently provide a signal representative of the surface of the sample, for compensating signals derived from larger signals. This can be done, for example, by subtracting Raman features detected for the null spacing from Raman features detected for one or more larger spacings.

Using the arrangement of FIG. 2a as an illustration, it will be seen that any number of spatial offsets between the entry and collection regions may be used, for example from one up to ten or more offsets, with Raman features typically being detected during separate exposure time intervals for each offset. Although in FIG. 2a the entry region remains fixed relative to the sample and the collection region is moved, the entry region could be moved instead or as well as the collection region. The regions in FIG. 2a are essentially circular or elliptical in shape, typically determined by convenience of implementation of the delivery and collection optics, various other shapes may be used. In FIG. 2a none of the collection regions 16b-16d overlaps with the entry region, but some overlap maybe permitted.

Figure 2B:
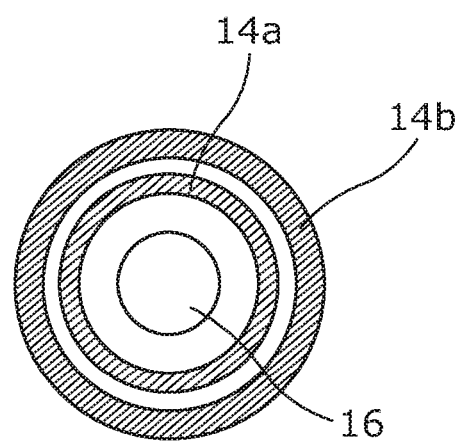

In FIG. 2b, a concentric arrangement is used in which a central collection region 16 lies within a surrounding entry region 14a, which could be in the form of a continuous or broken annulus. This has an advantage in that the entry region is relatively large, and therefore can be provided using a lower intensity of illumination to avoid damaging the sample. Multiple spatial offsets can then be provided by varying the radius of the entry region, as depicted by concentric entry regions 14a and 14b.

In order to provide sufficient scattering of the probe light to be able to detect Raman spectral features originating at depth with the sample, the sample may be a diffusely scattering or turbid or strongly diffusing. The degree of such scattering will depend on the sample, and may be defined in terms of transport length which is a length over which the direction of propagation of photon of probe light is randomized. The transport length I* may be taken as being related to the mean free path by the expression:

$$l^* = \frac{l}{1-g}$$

where g is the asymmetry coefficient (average of the scattering angle over a large number of scattering events), and I is the mean free path. The transport length for samples suitable for use with the present invention may be of the order of 1 mm for human or animal tissue, of the order of 100 µm for powders such as those from which pharmaceutical tablets are comprised, a few times 100 µm for uPVC materials and similar plastics, and so forth. To this end, the invention may apply to samples and volumes of samples in which the transport length is less than about 3 mm, or less than about 0.3 mm To this end, the invention may typically therefore be used with one or more spatial offsets between the entry and collection regions ranging from about 1 mm to about 50 mm, and more typically from about 3 mm to about 20 mm, and for determining temperature are depths within the sample of in the range from about 1 mm to about 30 mm and more typically from about 2 mm to about 15 mm. Embodiments of the invention may be arranged to determine temperature at just one depth or depth profile, for example using a single spatial offset between the entry and collection regions, or may be arranged to determine temperature at each of multiple depths or depth profiles. Embodiments may also use a zero or null offset in order to determine a temperature at the surface of the sample FIGS. 1, 2A and 2B depict entry and collection regions which are adjacent, proximal, or spaced apart on a surface which is largely planar or only moderately curved. Such an arrangement may be described as a backscatter configuration, because after penetrating into the sample and undergoing Raman scattering in a sub-surface region, a photon of probe light is backscattered to the surface of the sample for collection by the collection optics. However, the entry and collection regions may also lie on parts of the surface which are far from coplanar, with substantially different surface normals, for example with normals in the region of 90 degrees apart, or even in the region of 180 degrees apart, or any other angle or range of angles.

Figure 3:
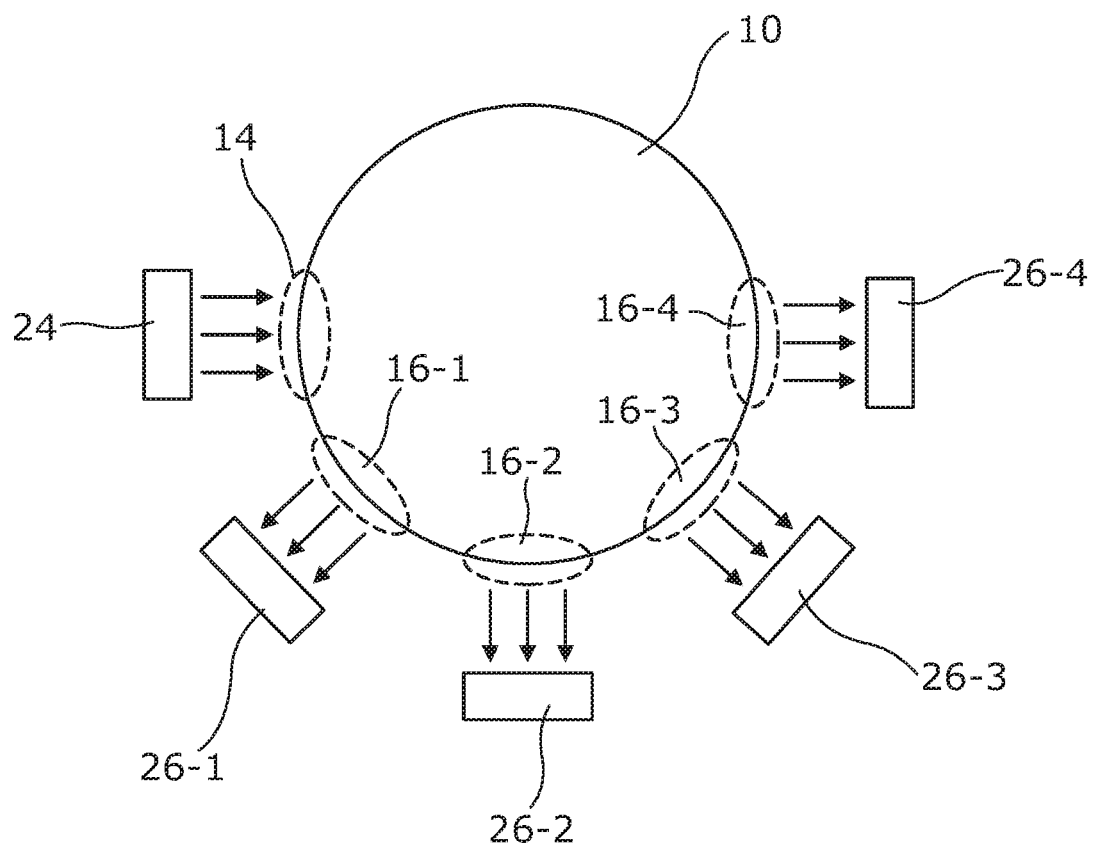
FIG. 3 shows how entry and collection regions may be disposed at different positions around a sample, for example in one or more transmission configurations.

For example, the entry and collection regions may be disposed on opposite sides of a sample, or such that a subsurface volume the temperature of which is being determined by the invention lies directly between the entry and collection regions, and such arrangements may be described as transmission configurations. An example of a transmission configuration is provided in FIG. 3. In this figure, delivery optics 14 define an entry region 14 on one side of a sample 10. Four different positions for collection optics 26-1-26-4 are then shown in the figure to form four different collection regions 16-1-16-4. The collection region 16-4 is on an opposite side of the sample 10 from the entry region, whereas the other collection regions 16-1-16-3 are spaced at angles of about 45, 90 and 135 degrees about the sample from the entry region. In such an arrangement, just one entry and one collection region could be used, or either or both or multiple entry and multiple collection regions may be used.

Transmission arrangements in which material of the sample lies directly between the entry and collection regions may be of particular interest where the sample is small, for example being only of the order of about 5 mm to about 50 mm in diameter or thickness for strongly scattering samples, although larger diameters or spacings between entry and collection regions could be used for more transparent samples.

Further discussion of transmission geometries and other details of such arrangements which can be used in embodiments of the present invention, to determine temperature of a sub-surface region of a sample, can be found in the prior art including WO2007/113566, the contents of which is incorporated herein by reference in it's entirety, to demonstrate how to arrange suitable transmission geometries for use in the present invention, and for all other purposes.

Figure 4:
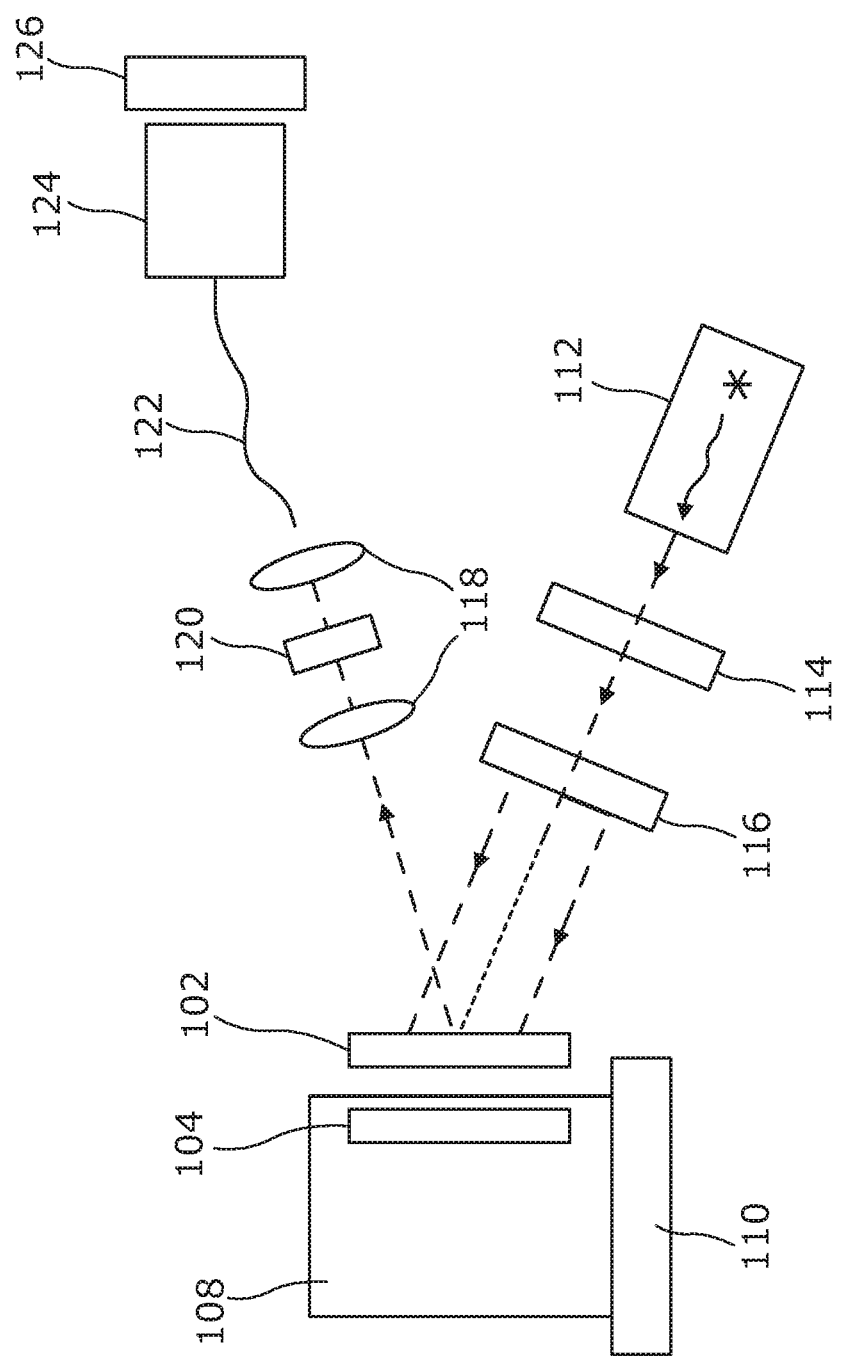
FIG. 4 shows an experimental arrangement for demonstrating the invention.

The principle of spatially offset Raman spectroscopy is based upon the concept that when Raman spectra of diffusely scattering media are collected at a location that is separated by a distance Δs from the laser illumination, the signal generated contains contributions from the materials buried beneath the surface of the material being probed. The larger the value of Δs the larger the relative contribution of the signals from the buried regions of the sample. FIG. 4 presents a schematic diagram of an experimental setup used to demonstrate the present invention for temperature measurements in a sub surface volume of a sample. The sample of FIG. 4 is provided by a layer of polyoxymethylene (POM) 102 about 3 mm thick, separated from a layer of polytetrafluoroethylene (PTFE) 104 also about 3 mm thick, by an air gap 106 of about 5 to 7 mm.

The PTFE layer was held in a quartz cell water bath 108 with a thermostatically controlled elevated temperature provided by heater 110. The POM layer was maintained at close to ambient temperature by the use of the air gap 106. Temperature in the quartz cell was measured using two type K thermocouples connected to a Pico—TC-08 thermocouple data logger. The water bath temperature was measured every second during experiments and the average temperature from the two thermocouples was used. Thermal images were also acquired using an FLIR i7 thermal camera.

The POM layer 102 was moved into and out of its experimental position using a Standa (8MTF) motorized xy stage. This allowed the measurements of PTFE Raman spectra without the POM layer where necessary.

The optics of FIG. 4 were arranged to provide an entry and a collection region similar to those illustrated in FIG. 2b, with an annular entry region surrounding a central collection region, and using a single spatial offset. The optical source was provided by a spectrum stabilised laser 112 with an excitation wavelength of 830 nm in combination with three 830 nm band pass filters 114 to provide a cleaner probe light spectrum. The delivery optics used an axicon lens 116 to provide the ring shaped entry region. The collection optics were provided by a matched pair of lenses 118, a notch filter 11 to exclude the excitation wavelength, and a fibre optic bundle 122 to guide the collected probe light to a spectral analyser comprising a Kaiser spectrometer 124 (Holospec 1.8i) using a deep depletion CCD camera 126 (Andor iDus-420) to collect the Raman spectra 126.

Each Raman spectrum was collected over a total exposure time of 60 seconds (made up of 12 separate acquisitions). For experiments carried out over a temperature range of 24 to 45 degrees Celsius, four repeat experiments each taking five spectra were used, at each of six temperature points, with the PTFE layer 104 being varied in temperature in 3.5 degree increments, and allowing the temperature to stabilize for 30 minutes between measurements. Further experiments were also carried out over a much smaller temperature range of about 2 degrees Celsius in approximately 0.5 degree increments.

Figure 5:
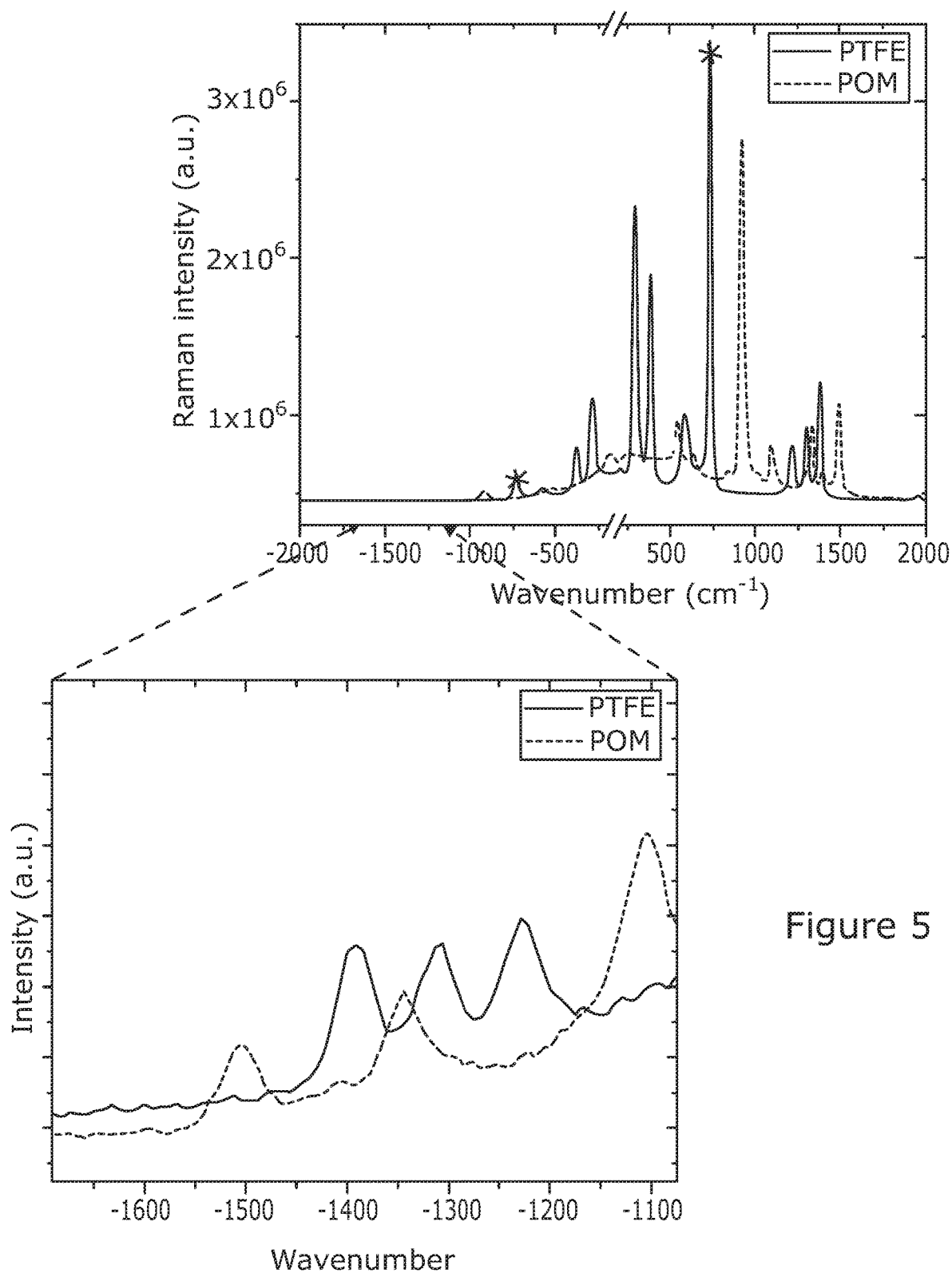
FIG. 5 illustrates Stokes and anti Stokes portions of spectra of PTFE and POM polymers used in the experimental arrangement of FIG. 4.

FIG. 5 shows room temperature measurements of the Raman spectra of the two diffusely scattering materials PTFE and POM, when measured independently. Both materials have Raman bands in the range of 200-1500 cm$^{-1}$, and these were all detectable in the anti-Stokes region of the spectrum on the inverse SORS system, albeit at a diminished intensity (relative to the Stokes region) as expected at room temperature. As is seen in the spectra, both materials have Raman bands that overlap, in addition to non-overlapping bands. To simplify analysis in these experiments, non-overlapping Raman bands of the sublayer PTFE at about +−750 wavenumbers were chosen (marked with asterisks) for determining the anti-Stokes/Stokes ratios.

Figure 6:
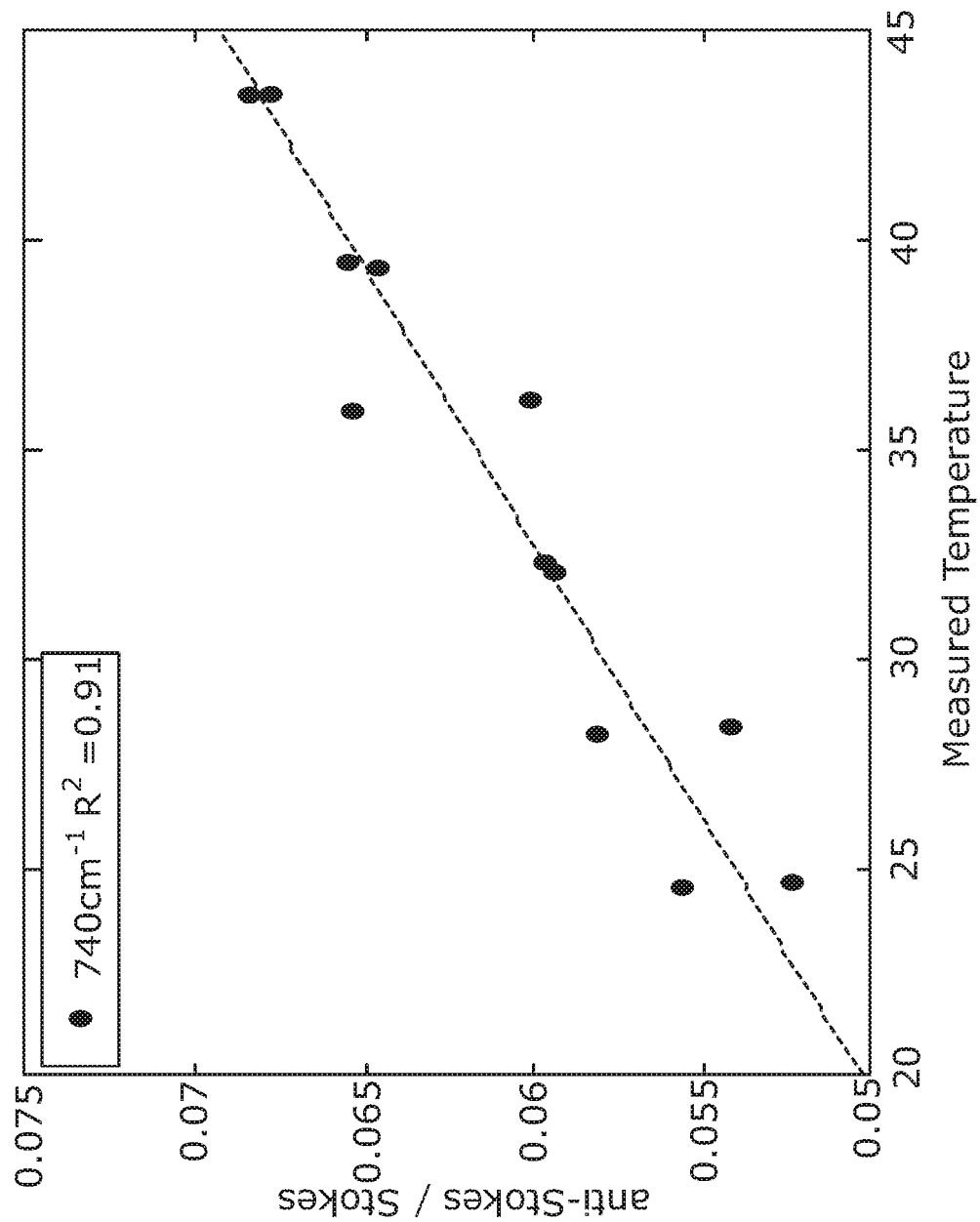
FIG. 6 is a graph of thermocouple measured temperature of the PTFE sample in FIG. 3 plotted against the ratio of intensities a particular pair of corresponding Stokes and anti Stokes spectral features.

FIG. 6 shows a calibration curve 150 derived as a least squares fit between the ratio of intensities of the Stokes/anti-Stokes bands plotted in the ordinate to measured temperature plotted in the abscissa. It can be seen that the calculated calibration curve obtained enables determination of the temperature in the test set of measurements for the sublayer PTFE from the relative intensities of the chosen Raman band to less than about 3° C. root mean squared error, RMSE.

The approach illustrated in FIG. 6, using an intensity ratio of a single pair of Stokes/anti Stokes features makes use of only a small portion of the available spectral information. Therefore, to evaluate whether making use of the whole spectrum for temperature prediction was able to improve the precision of the method, a multivariate method of partial least squares (PLS) was used. PLS is a commonly used method in chemometrics for both regression (PLS-R) and discriminant analysis (PLS-DA). It is a multivariate technique and so takes into account all variables simultaneously. The PLS algorithm extracts a number of latent variables from a training data matrix such that they contain the maximum variation that is covariate with a response variable (e.g. concentration for regression), in this case temperature of the PTFE layer.

In constructing a PLS model it is desirable to select an optimal number of components: too few and the model could be underfit, while too many can lead to overfitting, either of which can lead to a poor predictive ability. Here a leave-every-other-replicate-out PLS model was constructed from replicate sets of experimental data. The number of PLS components verses the percentage of explained variance showed that most of the variance was explained within the first five components.

Figure 7:
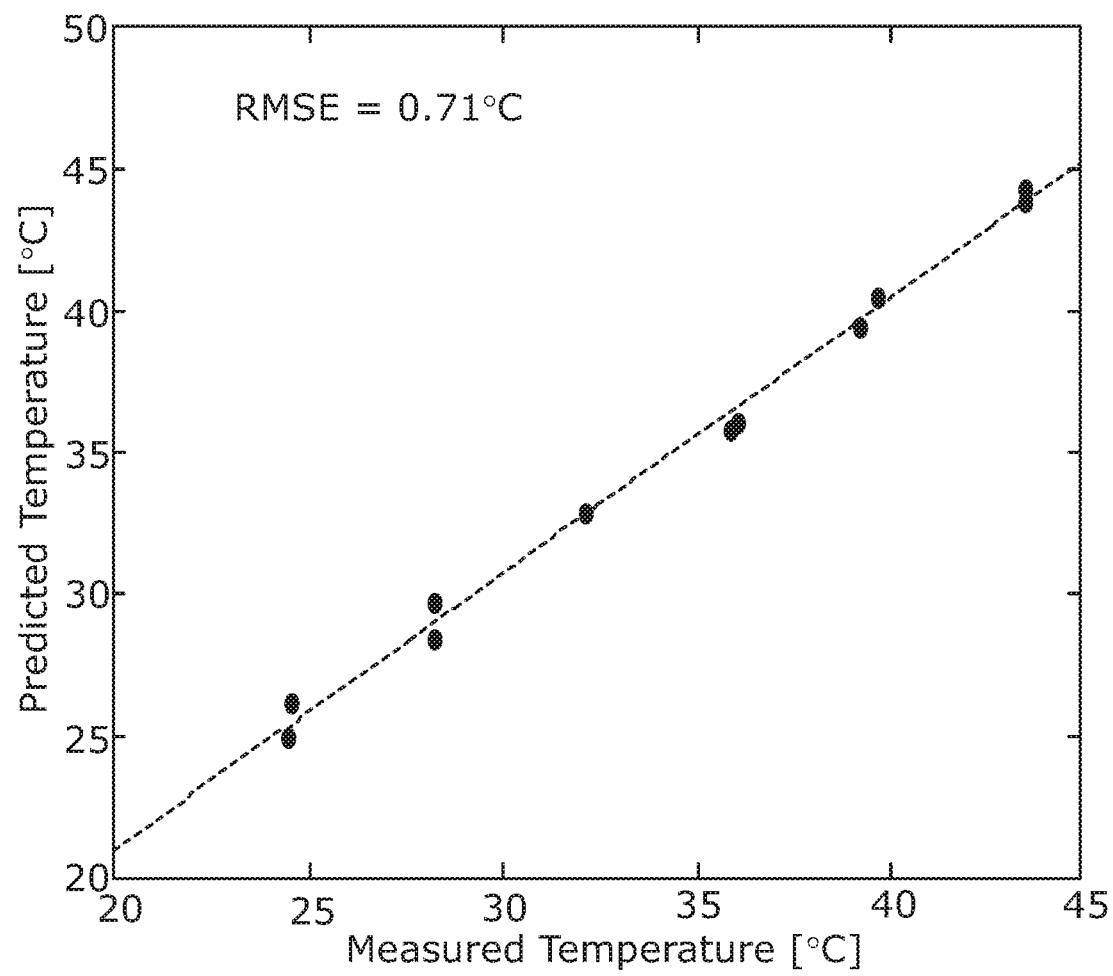
FIG. 7 is a graph of thermocouple measured temperature against temperature determined from Stokes and anti Stokes spectral features using a partial least squares model.

FIG. 7 shows the results using the constructed PLS model on the data not used for training. The constructed model shows a close fit of temperature predicted from the spectra with the thermocouple measured temperature, with an R2 value of 0.99, and as seen in FIG. 6 the prediction accuracy is improved, when tested on the test set of data, achieving a much lower RMSE of 0.71° C.

Figure 8:
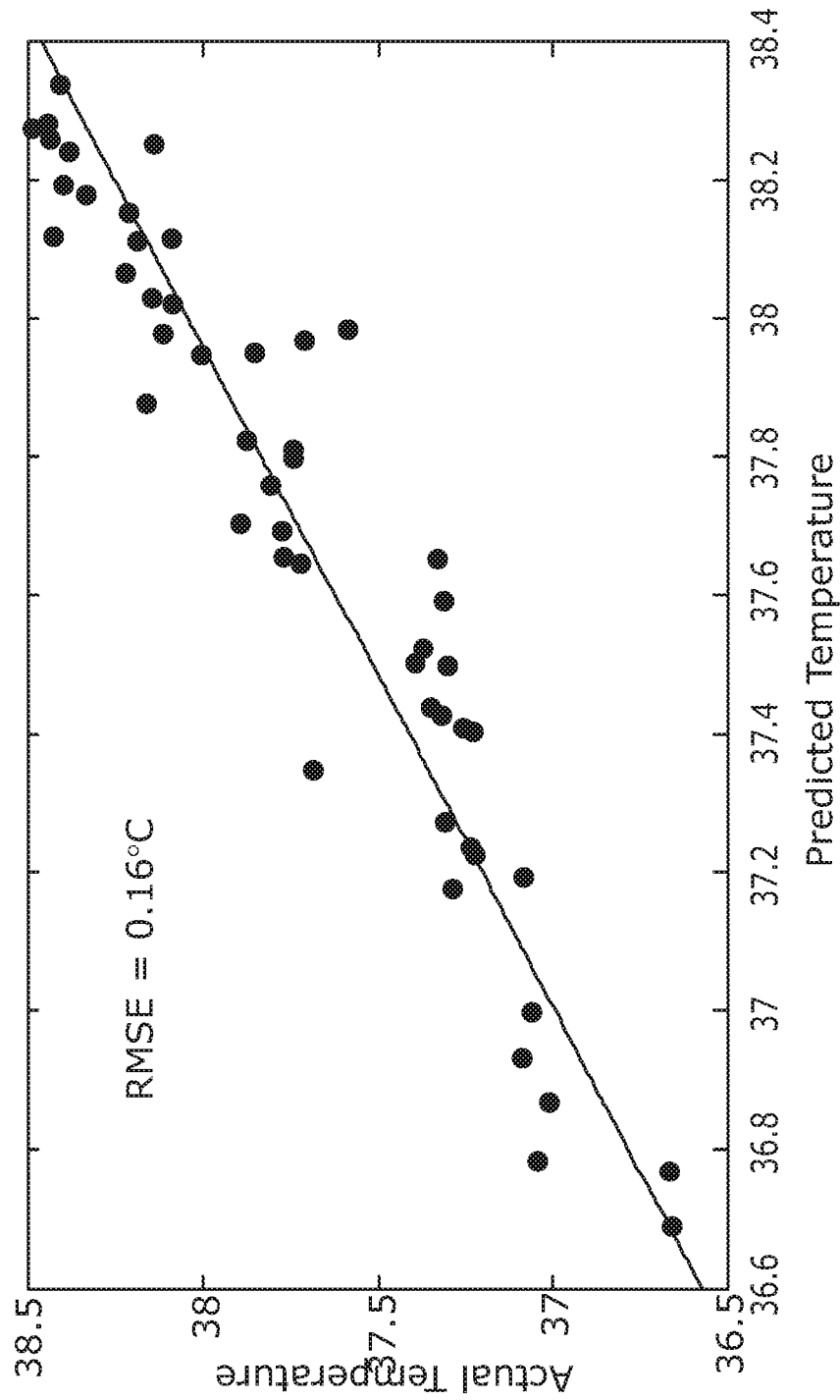
FIG. 8 is a graph similar to FIG. 7, but from an experiment using smaller temperature steps to collect data for generating the PLS model, and over a smaller temperature range.

To further demonstrate embodiments of the invention in measuring temperature of a subsurface samples over temperature ranges of particular clinical relevance, a much smaller temperature range was investigated. In this experiment, the temperature of the PTFE layer 104 was incrementally increased in ~0.5° C. steps over a range of 36.5-38.5° C. A new PLS model was developed over the new temperature range, and again most of the variance (>98%) was found to be explained in the first 5 PLS components. A good fit was seen in the calibration set of data with R2=0.99. A plot of temperature determined from the Raman spectra not used to train the data, against thermocouple measured temperature, is shown in FIG. 8. An RMSE of 0.16° C. was achieved. This improvement of the RMSE of prediction from 0.71 to 0.16° C. may partly be attributed to the much smaller 0.5° C. increments in temperature used. This result is of particular medical relevance as it encompasses clinically relevant values of subsurface temperatures.

In the text above, the invention has been discussed both in general terms and in terms of a thermometer suitable for clinical use. Further discussion of clinical areas, and of a variety of other areas of application of the invention will now also be presented.

Body core temperature monitoring may be used for a variety of purposes including to monitor intraoperative hypothermia, prevent patient overheating, and to facilitate detection of malignant hyperthermia. For example, core body temperature may be monitored by detecting the temperature of blood in the temporal artery, for example when a patient in under anaesthesia. The present invention may be used in such applications, by non-invasively detecting subcutaneous temperature, for example temperature in the region of or within an artery such as the temporal artery.

Detecting thermal stress can also be an important part of neonatal care. core temperature may vary between different tissues, for example being higher in the brain. Embodiments of the present invention may be used to detect and monitor neonatal body core temperature in various tissues non-invasively, as well as optionally measuring peripheral temperature. Both of these functions can operate without contact with the patient, thereby reducing biological risks.

Other medical areas which may benefit from sub-surface temperature detection using the present invention include joint inflammation, diabetic limb (for example foot) screening, and Reynaud's syndrome screening. Other medical applications include monitoring the temperature of organs during transport, and modulating freezing rates during cryopreservation, with such applications benefiting from the ability to monitor sub-surface temperatures non-invasively, and without contact with the apparatus for detecting temperature.

Figure 9:
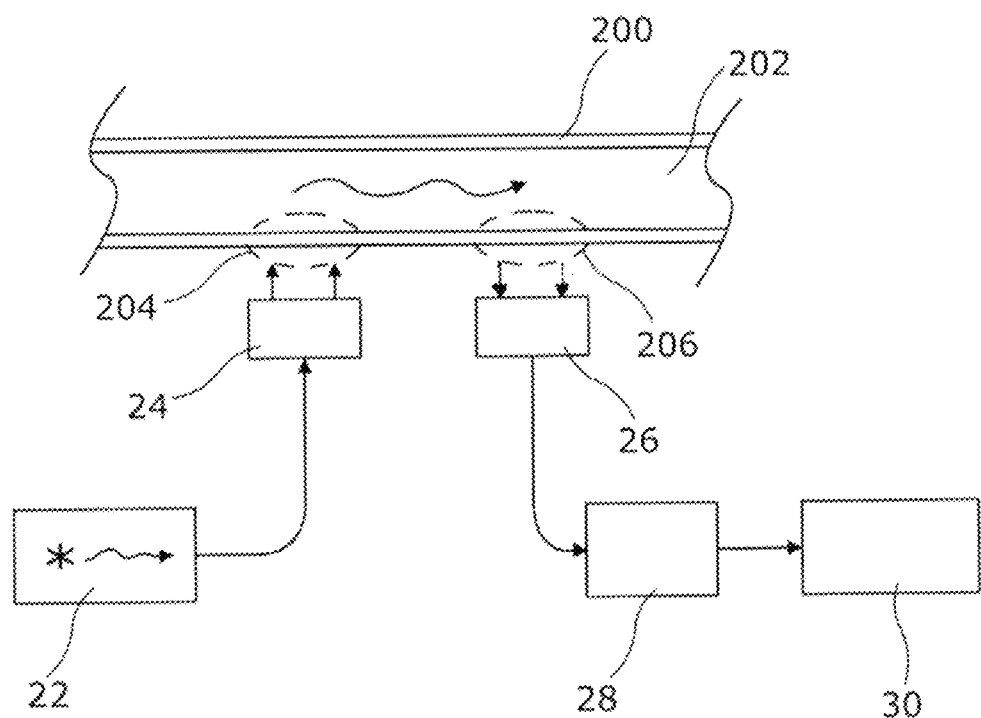
FIGS. 9 and 10 show how the invention may be applied to a conduit or other vessel containing a fluid.

Embodiments of the invention may also be used in various medical areas involving temperatures of samples outside the body. FIG. 9 illustrates a conduit 200 such as a pipe or tube along which a fluid 202 is flowing. The conduit 200 is transparent or translucent to probe light delivered to an entry region 204 on a surface of the conduit by suitable delivery optics 24, such that the probe light at least partly passes through the conduit 200 and into the fluid, where Raman scattering of the probe light takes place. Scattered probe light passes out of the fluid 202 through the conduit, passing through a collection region 206 to be collected by collection optics 26 such that the entry region 204 is spaced from the collection region 206. Multiple spacings between the entry and collection regions may be used if required as already described above. Instead of the conduit 200 as a whole being transparent or translucent, the conduit 200 may be provided with one or more suitable windows transparent or translucent to the probe light, upon which the entry and collection regions may be formed.

FIG. 9 also shows a probe light source 22, a spectral analyser 28 and a processor 30 as already described in respect of earlier figures. The spectral analyser 28 detects Stokes and anti-Stokes Raman features (which may for example be corresponding specific features or corresponding spectral regions) and the processor 30 uses these features to determine a temperature of the fluid 202 within the conduit 200.

Figure 10:
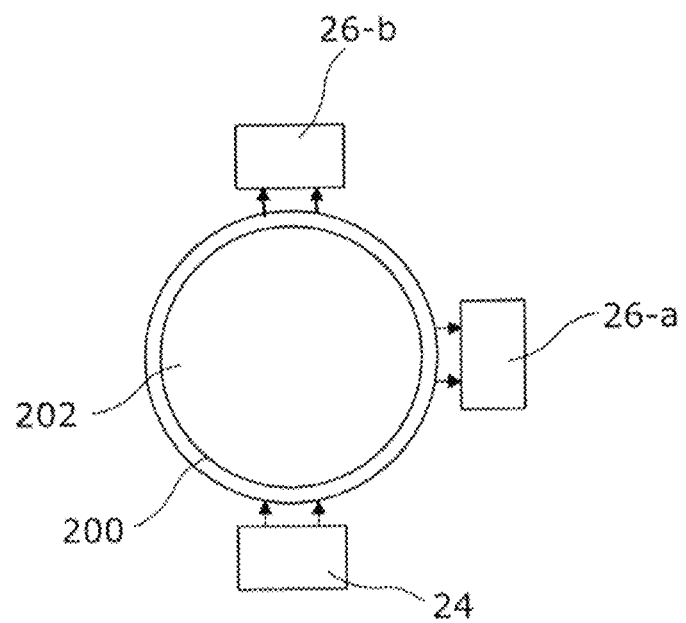

Although the entry and collection regions of FIG. 9 are shown as being spaced along an axial direction of the conduit, they may be spaced in other ways for example as shown in FIG. 10, where a first example collection region 26-a is shown spaced at a first angular offset in respect of the conduit axis (in this case at 90 degrees), and a second example collection region 26-b is shown spaced at a second angular offset (in this case at 180 degrees).

Arrangements such as those shown in FIGS. 9 and 10 may be used in a variety of medical applications where fluids are to be processed outside the body, and temperature of those fluids needs to be monitored. Temperature measurement using the present invention has the advantage of not requiring any contact with the fluid 202 in the conduit, thereby avoiding risk of contamination. Moreover, the depth within the conduit 200 at which the fluid temperature is monitored can be adjusted or varied by controlling the spatial offset between and other properties of the entry and collection regions. To this end, the conduit 200 may form part of, for example, a transfusion system, an IV warming system, a dialysis system, a cardio-pulmonary bypass system, and ECMO system, or a blood analyser. The fluid 202 in the conduit could therefore be blood or blood components, fluid to be administered intravenously, etc.

In some embodiments, the conduit 200 could instead be a vessel or container within which a fluid (such as blood or a fluid for intravenous use) is to be contained, and the invention may then be used to determine a temperature of the fluid in the same way.

Figure 11:
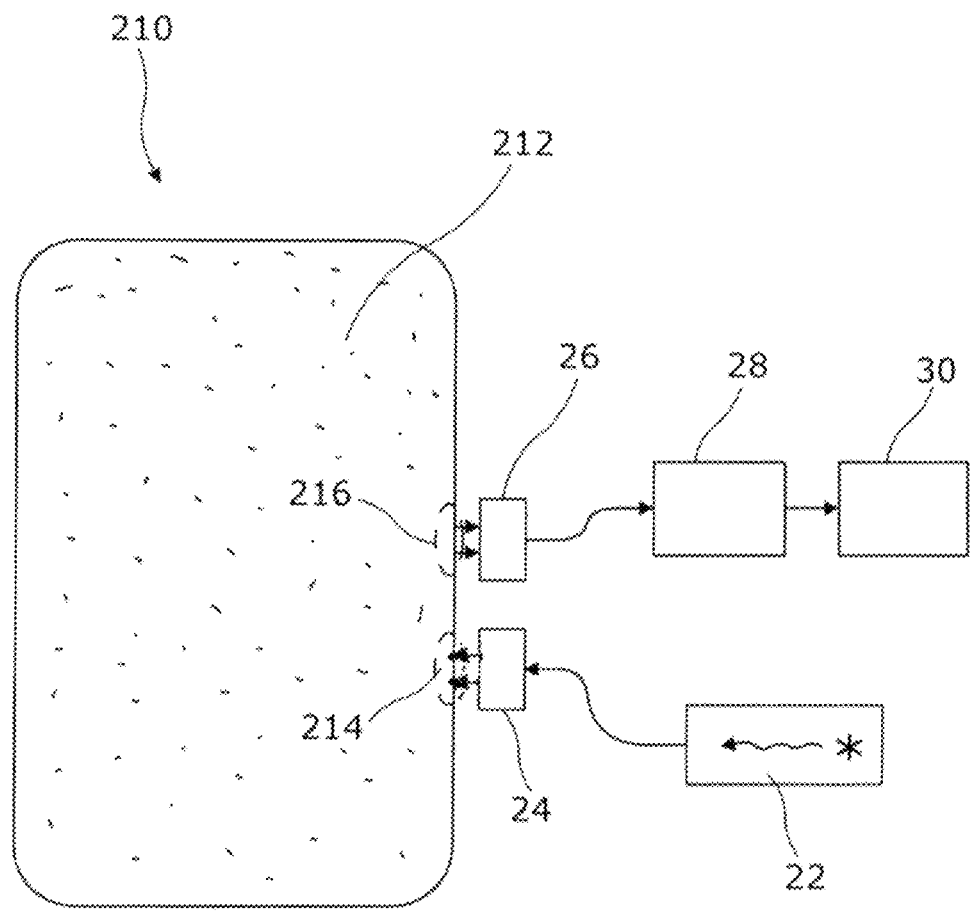

The invention may also be used to provide non-invasive temperature measurement of reagent fluids contained within bioreactors, thereby providing detection of temperature at depth within the reagent fluids without risk of contamination. To this end, FIG. 11 illustrates schematically a bioreactor 210 containing reagents 212 retained within a vessel wall 213. Apparatus as described elsewhere in this document is provided to determine a temperature of the reagents, by providing an entry region 214 and a collection region 216 on the vessel wall. For example, the vessel wall may be transparent or translucent, or the entry and collection regions may be provided on suitable windows in the vessel wall.

The bioreactor 210 may be, for example, a stirred tank reactor, an airlift reactor, a packed bed reactor, a fluidised bed reactor, a photobioreactor, a membrane bioreactor, a rotary drum reactor, and/or a single use bioreactor, part of a rocking motion or stirred tank system, or any vessel system/configuration that supports a biologically active environment.

Bags and single-use bioreactors are in the process of revolutionising the way biopharmaceuticals are manufactured. Since its introduction more than 10 years ago, single-use bioreactor technology has now become an established addition to today's biotechnology manufacturing facility. Many single-use options are available, each with its advantages and disadvantages, although scalability is often promoted as one of the biggest general limitations. One of the biggest advantages of single-use bioreactors is flexibility. The increasing trend towards multi-drug facilities demands the production of different drugs using the same facility, with minimum time and cost, without compromising the quality of the drug. The development of robust and accurate single-use sensor technologies will speed up the adoption of fully single-use bioreactors. Wave-induced motion SUBs form the largest segment of the SUB market. Biologics manufacturing is expected to be the fastest-growing end-user segment for this market.

Embodiments of the invention may also be used in food processing such as dough mixing, microwave heating, frozen food products, baking and so forth, to remotely detect sub surface temperature of a food product or food component without risk of contamination. For example, measuring the temperature of bread and pastry dough while mixing is difficult at best with conventional contact thermocouple probes, due to breakage and possible contamination of the food. However, the temperature is quite important since too high a temperature will cause too much rise, leading to holes in the baked product, and too low a temperature will not allow the dough to rise sufficiently, resulting in a product that is flat. To this end, the sample illustrated in FIG. 1 may be a food product or component, and such a product or component may be contained within a suitable vessel, conduit or other container as illustrated in FIGS. 9, 10 and 11 and in other ways.

Figure 12:
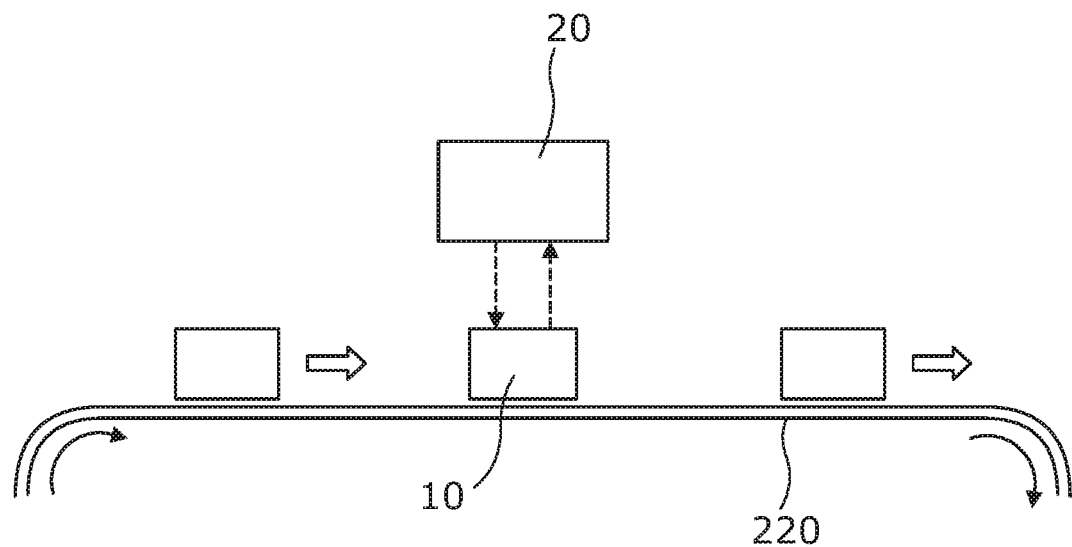
FIG. 12 shows the invention applied to detecting sub-surface temperature of moving sample objects, for example along a conveyor.
Figure 13:
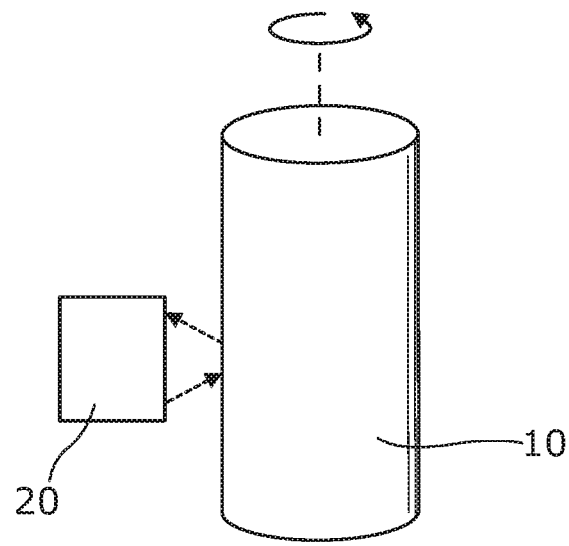
FIG. 13 shows the invention applied to detecting sub-surface temperature of a rotating object.

FIG. 12 shows how apparatus 20 for measuring temperature in a sub-surface volume of a sample 10 may be provided to determine sub-surface temperature in a plurality of sample objects 10 moving relative to the apparatus, for example being carried along a conveyor 220 of a manufacturing or processing production line, or otherwise being passed along a path past the apparatus. FIG. 13 shows how apparatus 20 for measuring temperature in a sub-surface volume of a sample 10 may be provided to determine sub-surface temperature in a sample object 10 which is rotating relative to the apparatus, whereby the apparatus 20 may determine temperature of a sub-surface portion of the sample 10 which is located proximally to the apparatus at any particular time Temperature measurement also plays an important role in many industrial chemical processing facilities. Industries in which the present invention may conveniently be used include Oil & Gas, Chemicals, and Power & Energy. In the field of sintering of materials, accurate control of the temperature inside heated parts is necessary to avoid local melting or distortions. Plastic sintering is used to create filters that are of high strength, resistant to chemicals and lightweight. During the sintering process, temperature measurement in the microwave cavity is known to be problematic, but can be carried out using the present invention by defining entry and collection regions on the surface of the plastic and carrying out optical and other operations as already described above.

Temperature measurement according to the present invention may also be used in semiconductor manufacture processes, for example in low temperature vacuum and deposition processes to enable continued reduction of feature size and improvements in functionality of semiconductor products. In the prior art, infrared thermometry is a widely used measurement technique in such processes. However, the emissivity of silicon and other semiconductor materials is extremely low in the infrared region, with emissivity based temperature measurements becoming too inaccurate for practical use below about 200 degrees Celsius. Semiconductor materials to which techniques of the invention may be applied for measuring sub-surface temperature include germanium, gallium arsenide, silicon carbide, and many more.

Figure 14:
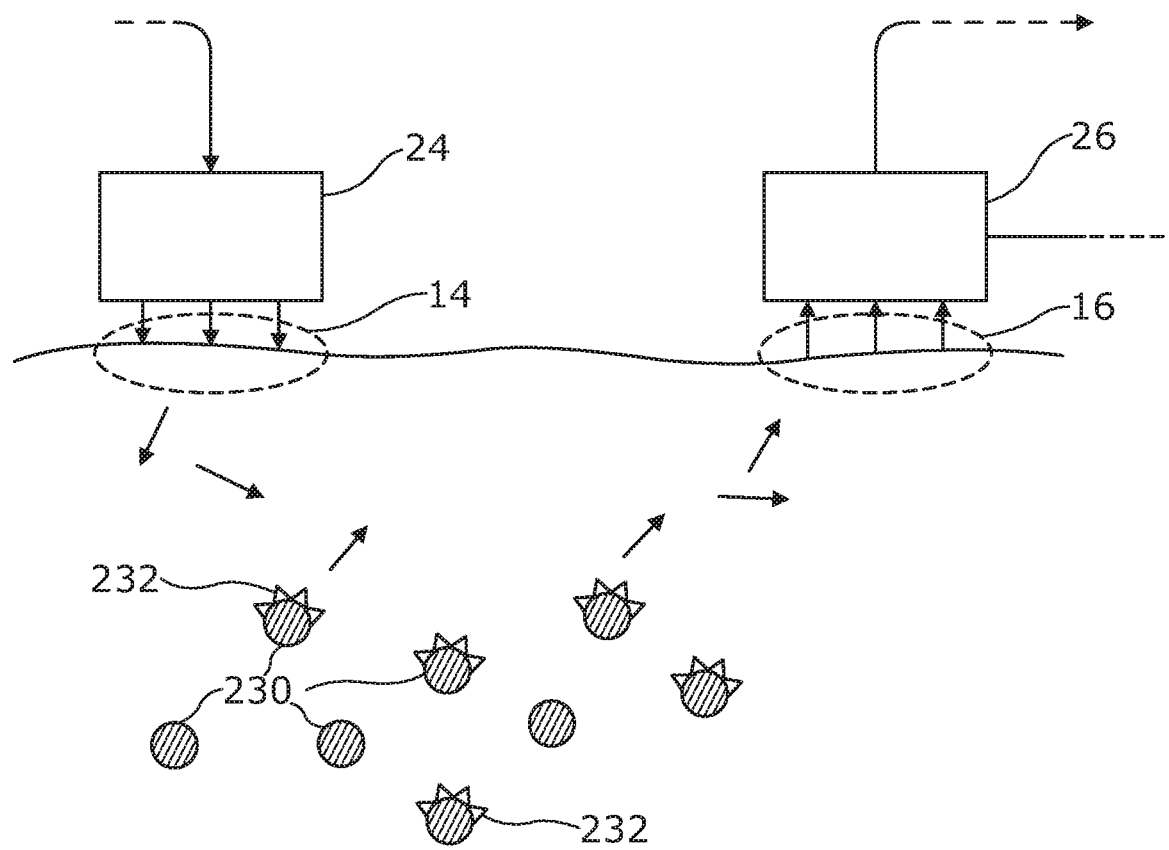
FIG. 14 is similar to FIG. 1, but showing detection of subsurface temperature using Surface Enhanced Raman Spectroscopy (SERS) by providing SERS substrates within the sample volume where temperature is to be determined.

FIG. 14 illustrates other ways in which the invention may be implemented using Surface Enhanced Raman Spectroscopy techniques. FIG. 14 is based on FIG. 1, but for convenience and clarity omits many elements of that figure, although such elements may be used in the arrangement of FIG. 14 and similar embodiments.

In particular, the arrangement of FIG. 14 includes within the sub-surface volume of the sample one or more Surface Enhanced Raman Spectroscopy (SERS) substrates 230. These SERS substrates 230 are selected or designed to increase, often by many orders of magnitude, Raman scattering cross sections of chemical entities proximal to the surfaces of these substrates. The SERS enhancement of Raman scattering cross sections may be strongly wavelength dependent, so that careful selection or design of suitable SERS substrates in order to enhance particular Raman spectral features may be required. SERS substrates may typically include nanoparticles, such as nanospheres, with metallic surfaces disposed on non-metallic cores, or formed entirely of suitable metals, typically gold or silver. Such nanoparticles may be provided as a colloidal solution, for example for injection into a sample such as human or animal tissue to be investigated using SERS. However, SERS substrates may instead be provided by a surface carrying suitable nanoscale structures, such as a silicon or glass surface with a nanostructured noble metal surface such as electrochemically roughened silver.

The apparatus of FIG. 14 is arranged to detect one or more SERS Raman spectral features arising from Raman scattering 232 at the SERS substrates within the subsurface volume, and to determine a temperature of the subsurface volume using those SERS Raman spectral features, for example using differences between corresponding Stokes and Anti-Stokes features found in the collected light resulting from that SERS Raman scattering 232, such techniques having already been described above for none-SERS arrangements.

To demonstrate the effectiveness of this technique, the inventors carried out SERS experiments using gold nanoparticles carrying 4-Mercaptobenzoic acid (MBA) to determine the relationship between Stokes / anti-Stokes ratio and temperature. 1 ml of 0.025 mg/ml Citrate coated gold nanoparticles were mixed for five minutes with 100 μl of 1mM MBA in ethanol, and then centrifuged at 3000 rpm for ten minutes. The supernatant was removed and the remaining material was resuspended in phosphate buffered saline. This preparation was repeated with nanoparticles of four different sizes: 40, 60, 80 and 100 nm.

Figure 15:
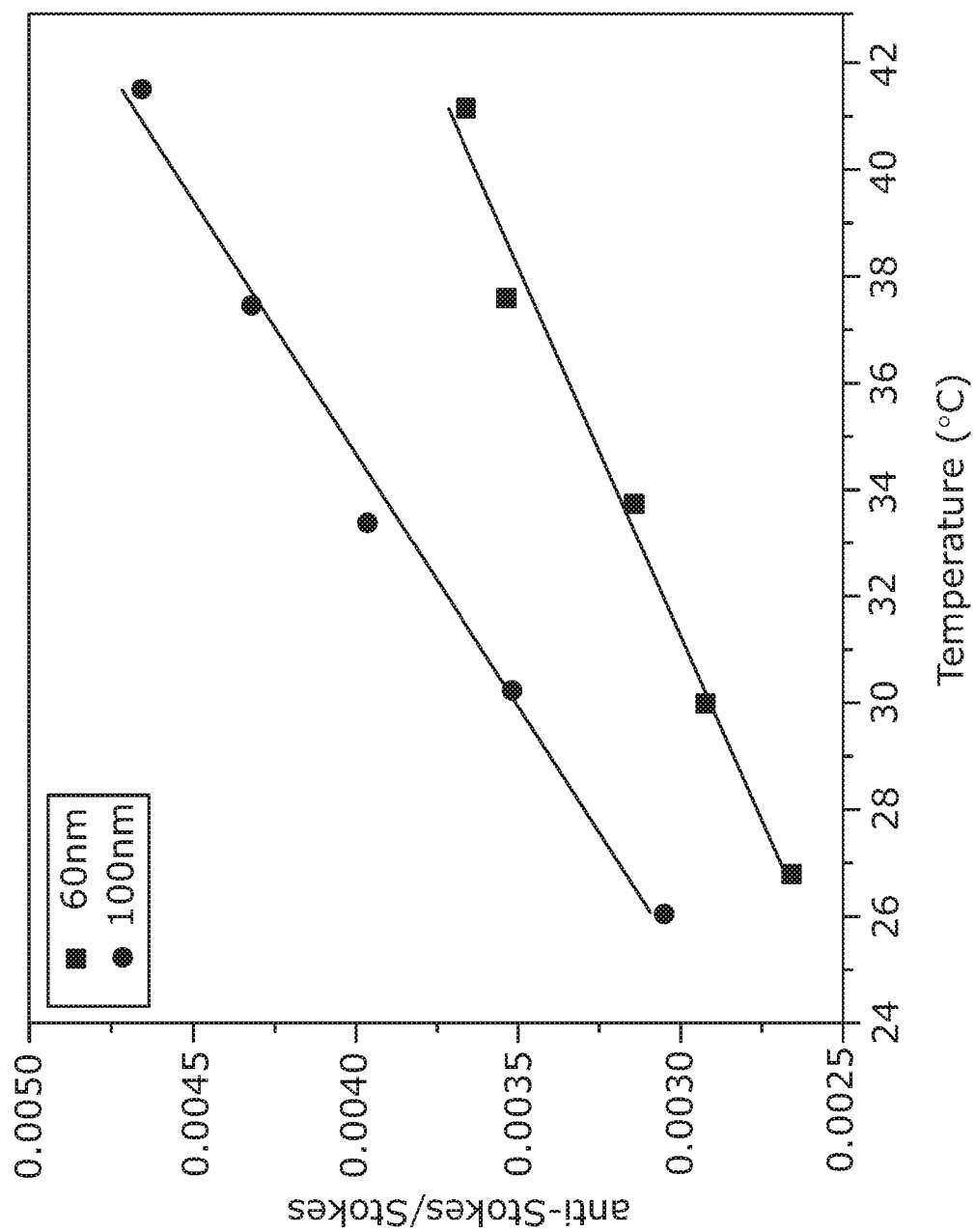
FIG. 15 shows experimental relationships between the anti-Stokes / Stokes ratio of SERS spectral features and temperature of the solution in which the SERS substrates are suspended.

FIG. 15 shows plots of the ratios of corresponding anti-Stokes and Stokes peaks at a Raman shift of about 1580 $cm^{-1}$, against ambient temperature of the tested solution, for the 60 and 100 nm particle sizes described above, showing a strong and approximately linear dependence upon temperature over the tested range of about 26 to about 42 degrees Celsius. These or similar nanoparticles can readily be used in a subsurface volume of a suitable sample for detecting a temperature associated with the SERS Raman scattering in that subsurface volume, by applying the various techniques described in this document. Clearly, various other sizes, shapes and types of SERS substrates 230 can similarly be selected and used according to requirements such as the particular Raman spectral features which are to be detected and the nature of the sample. For example, nanoparticles in solution may be a suitable for delivering to a subsurface tissue of a human or animal subject, by injection or in other ways, and separate nanoparticles could similarly be dispersed within a diffusely scattering substrate for other purposes. These techniques can also be chemically specific by arranging for particular target molecules to bind to the surface of the SERS substrates, so that their proximity to the substrates leads to a very strong Raman signal specifically from these target molecules. Application areas where this may be of particular benefit include subsurface temperature monitoring in treatments in vivo, and subsurface monitoring of temperature in industrial processes involving turbid samples.

Some embodiments of the invention make use of the described techniques to detect sub surface or subcutaneous temperature in implementations of thermal therapies, in which a region of human or animal tissue is heated for treatment or therapy, for example in order to damage or destroy cancer cells, tumours or other undesired regions of disease, or to activate or increase the effectiveness of a drug or other mode of treatment. In particular, embodiments of the invention may make use of the described techniques in implementations of photo thermal therapy, and more particularly in plasmonic photo thermal therapy in which nanoparticles or other suitable plasmonic heating substrates are injected or otherwise disposed in a region of tissue, and electromagnetic radiation, commonly in the near infrared spectral region is used to heat the heating substrates remotely. However, the invention may also be used to detect sub surface or subcutaneous temperature in implementations of other thermal therapies, for example in radiofrequency or thermal therapies or proton therapies.

Figure 16:
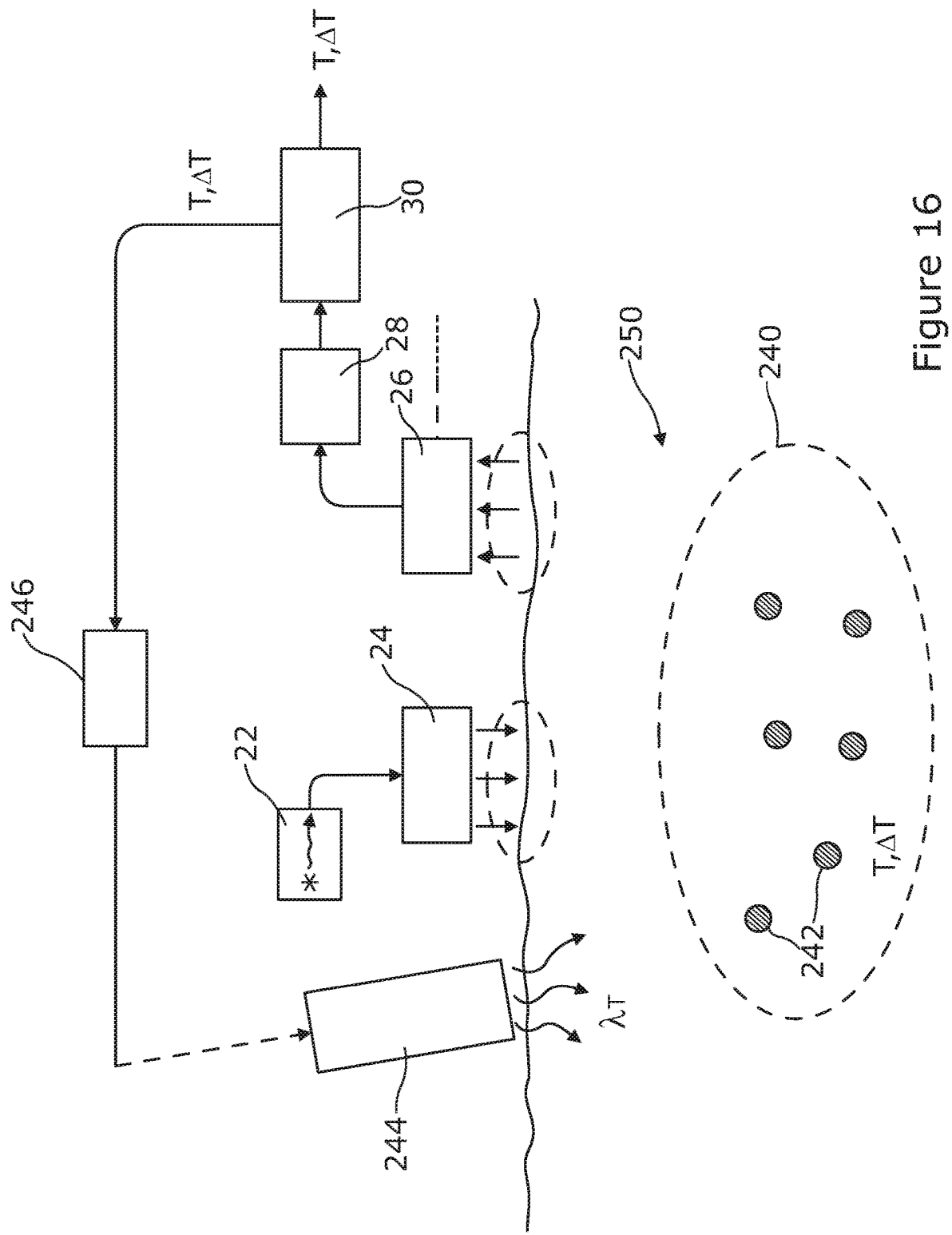
FIG. 16 illustrates how embodiments of the invention may be used in conjunction with thermal therapies, and if the thermal therapy uses heating substrates in a region of tissue to be heated, the same or other SERS substrates may be used for determining and controlling temperature in that region.

By way of example, FIG. 16 illustrates apparatus and methods for plasmonic photo thermal therapy of a region 240 of tissue in a human or animal body 250. Heating substrates 242, such as suitably selected or designed metal or metal coated nanoparticles or microparticles, are provided in the region 240, for example by direct injection in a solution, by transport through the lymph system, blood supply or other transport mechanism, or in other ways. A heating light source 244 is then provided to direct heating radiation into the subject 250 so as to increase the temperature of the region for example by a temperature change such as ΔT, which may be controlled by various means such as by controlling the intensity of the heating radiation in the region 240.

The heating radiation is labelled in FIG. 16 as having a wavelength $\lambda_T$, but more than one wavelength or a range of wavelengths could be used, as long as the heating radiation can penetrate through the subject sufficiently to the region 240 to cause suitable heating of the region through interaction with the heating substrates 242. Typically the heating mechanism could be plasmonic heating although other heating mechanisms could instead or also be used.

In parallel with the heating of the region 240 using plasmonic photo thermal therapy, FIG. 16 illustrates the already described techniques of subsurface temperature detection being used to detect a temperature of the region 240 through spatial offset Raman spectroscopy. In this way, the temperature T or change in temperature ΔT in the region 240 can be calculated by processor 30 and output for monitoring by a clinician. The temperature T or change in temperature ΔT may also be output to a heating controller 246 which controls heating light source 244 in order to maintain temperature T or change in temperature ΔT (for example compared to a baseline or reference temperature) at a suitable level, for example at a temperature suitable for damaging the tissue region 240 while minimising side effects or damage to surrounding areas of tissue. More particularly, the heating controller 246 may be used to maintain the temperature of the tissue with a desired target range.

The operation of subsurface temperature detection in the arrangement of FIG. 16 and in similar thermal treatments and therapies may be implemented by detecting SERS Raman scattering 232 as already shown in FIG. 14. This can be achieved by using the same substrates in the tissue both as heating substrates 242 for heating by the heating radiation and as SERS substrates 230 for detecting temperature, and to this end, both the heating and the temperature detection may make use of the same wavelengths of radiation directed to the region, and be generated by a single or by common light sources, thereby combining probe light source 22 and heating light source 244 in FIG. 16. However, this can also be achieved by using different substrates in region 240 for the heating and SERS temperature detection process, with or with the same wavelengths of light for these processes.

Although particular embodiments and applications of the invention have been described, it will be apparent to the skilled person that various modifications and alterations can be made without departing from the scope of the invention.

The invention claimed is:

1. A method of measuring temperature in a sub-surface volume of a sample, comprising:
    directing probe light to an entry region on the sample surface;
    collecting said probe light from a collection region on the sample surface, following scattering within the subsurface volume of the sample, the collection region being spatially offset from the entry region;
    detecting one or more Raman spectral features in the collected probe light; and
    determining a temperature of the subsurface volume from the one or more Raman spectral features,
    wherein determining a temperature of the subsurface volume comprises determining a temperature of a particular chemical component present in the subsurface volume, by detecting Raman features characteristic of the particular chemical component, and by determining the temperature of the particular chemical component from the detected Raman features characteristic of the particular chemical component.

2. The method of claim 1 wherein determining a temperature of the subsurface volume from the one or more Raman spectral features comprises determining the temperature using differences between one or more Stokes features and the corresponding anti Stokes features in the detected Raman spectral features.

3. The method of claim 2 wherein determining the temperature using differences between one or more Stokes features and the corresponding anti-Stokes features comprises using ratios of said Stokes and anti-Stokes features.

4. The method of claim 1 wherein the subsurface volume comprises tissue of a human or animal subject, and the particular chemical component is present in the tissue due to being previously administered to the subject.

5. The method of claim 1 wherein the entry and collection regions are disposed on opposite sides of the sample.

6. The method of claim 1 comprising separately detecting said one or more Raman spectral features in the collected probe light for each of a plurality of different spatial offsets between said entry and collection regions.

7. The method of claim 6 wherein determining a temperature of a sub-surface volume from the one or more Raman spectral features comprises associating the Raman features from each of said plurality of different spatial offsets with a different depth or distribution of depth within the sample.

8. The method of claim 7 further comprising combining said Raman features from said different spatial offsets to determine a separate temperature for each of one or more depths or distributions of depth within the sample.

9. The method of claim 1 further comprising setting said entry and collection regions to be coincident or overlapping, and detecting one or more Raman spectral features in the collected probe light when said entry and collection regions are coincident or overlapping.

10. The method of claim 9 wherein determining a temperature of a subsurface volume from the Raman spectral features comprises compensating said Raman spectral features detected when the entry and collection regions are spatially offset using the Raman spectral features detected when the entry and collection regions are coincident or overlapping.

11. The method of claim 9 further comprising determining a temperature of the sample surface from the one or more Raman spectral features detected when the entry and collection regions are coincident or overlapping.

12. The method of claim 1, wherein each entry region has a shape in a form of a continuous or non-continuous annulus arranged concentrically around the collection region.

13. The method of claim 1, wherein the entry and collection regions are spatially offset by an offset in the range from 1 mm to 50 mm.

14. The method of claim 1 wherein the sample is a diffusely scattering sample.

15. The method of claim 1 wherein the sub-surface volume for which temperature is determined is diffusely scattering.

16. The method of claim 14,
    wherein the diffusely scattering sample or volume has a transport length of less than 3 mm;
    wherein the transport length is a length over which a direction of propagation of photon of probe light is randomized.

17. The method of claim 1 wherein the sub-surface volume comprises tissue of a human or animal subject, and the determined temperature is a sub-surface temperature of the tissue.

18. The method of claim 17 wherein the sample surface is a surface of skin of the human or animal subject.

19. The method of claim 1 wherein the method is a method of non-invasive measurement of a sub-cutaneous temperature of a tissue of the human or animal subject, and the entry region is a visible surface of the subject.

20. A method of measuring temperature in a sub-surface volume of a sample, comprising:
    directing probe light to an entry region on the sample surface;
    collecting said probe light from a collection region on the sample surface, following scattering within the subsurface volume of the sample, the collection region being spatially offset from the entry region;
    detecting one or more Raman spectral features in the collected probe light; and
    determining a temperature of the subsurface volume from the one or more Raman spectral features;

wherein the sample comprises a fluid within a containing wall, the entry and collection regions are provided on said containing wall, and the subsurface volume comprises a volume of the fluid; and wherein the containing wall comprises one or more windows, and the entry and collection regions are provided on said windows.

21. The method of claim 20, wherein the entry region and collection regions are disposed on opposite sides of the sample.

22. The method of claim 20,
wherein detecting one or more Raman spectral features in the collected probe light comprises separately detecting said one or more Raman spectral features in the collected probe light for each of a plurality of different spatial offsets between said entry and collection regions; and
wherein determining the temperature of the sub-surface volume from the one or more Raman spectral features comprises associating the Raman features from each of said plurality of different spatial offsets with a different depth or distribution of depth within the sample.

23. The method of claim 22 further comprising combining said Raman features from each of said plurality of different spatial offsets to determine a separate temperature for each of said different depth or distribution of depth within the sample.

24. The method of claim 20, wherein the sub-surface volume of the sample for which temperature is determined is diffusely scattering.

25. A method of measuring temperature in a sub-surface volume of a sample, comprising:
directing probe light to an entry region on the sample surface;
collecting said probe light from a collection region on the sample surface, following scattering within the subsurface volume of the sample, the collection region being spatially offset from the entry region;
detecting one or more Raman spectral features in the collected probe light; and
determining a temperature of the subsurface volume from the one or more Raman spectral features;
wherein the sample comprises a fluid within a containing wall, the entry and collection regions are provided on said containing wall, and the subsurface volume comprises a volume of the fluid; and
wherein the containing wall at least partly defines a conduit within which the fluid is flowing.

26. The method of claim 25, wherein the entry and collection regions are disposed on opposite sides of the sample.

27. The method of claim 25,
wherein detecting one or more Raman spectral features in the collected probe light comprises separately detecting said one or more Raman spectral features in the collected probe light for each of a plurality of different spatial offsets between said entry and collection regions; and
wherein determining the temperature of the sub-surface volume from the one or more Raman spectral features comprises associating the Raman features from each of said plurality of different spatial offsets with a depth or distribution of depth within the sample.

28. The method of claim 27 further comprising combining said Raman features from each of said different spatial offsets to determine a separate temperature for each of one or more depth or distribution of depth within the sample.

29. The method of claim 25, wherein the sub-surface volume for which temperature is determined is diffusely scattering.

30. A method of measuring temperature in a sub-surface volume of a sample, comprising:
directing probe light to an entry region on the sample surface;
collecting said probe light from a collection region on the sample surface, following scattering within the subsurface volume of the sample, the collection region being spatially offset from the entry region;
detecting one or more Raman spectral features in the collected probe light; and
determining a temperature of the subsurface volume from the one or more Raman spectral features;
wherein the sample comprises a fluid within a containing wall, the entry and collection regions are provided on said containing wall, and the subsurface volume comprises a volume of the fluid; and
wherein the containing wall is the wall of a bioreactor and the fluid comprises reagents within the bioreactor.

31. The method of claim 30, wherein the entry and collection regions are disposed on opposite sides of the sample.

32. The method of claim 30,
wherein detecting one or more Raman spectral features in the collected probe light comprises separately detecting said one or more Raman spectral features in the collected probe light for each of a plurality of different spatial offsets between said entry and collection regions; and
wherein determining the temperature of the sub-surface volume from the one or more Raman spectral features comprises associating the Raman features from each of said plurality of different spatial offsets with a depth or distribution of depth within the sample.

33. The method of claim 32 further comprising combining said Raman features from each of said different spatial offsets to determine a separate temperature for each of one or more depth or distribution of depth within the sample.

34. The method of claim 30, wherein the sub-surface volume for which temperature is determined is diffusely scattering.

35. Apparatus for measuring temperature within a volume of a sample having a surface, comprising:
a light source for generating probe light;
delivery optics arranged to direct the probe light to an entry region on the surface;
collection optics arranged to collect said probe light from a collection region on the surface, following scattering within the volume of the sample, the collection region being spatially offset from the entry region;
a spectral analyser arranged to detect Raman spectral features in the collected probe light;
a processor arranged to determine a temperature of the volume from the Raman spectral features; and
an offset driver arranged to provide a plurality of different spatial offsets between said entry and collection regions, the apparatus being arranged to separately detect said Raman spectral features for each different spatial offset, and to associate the Raman features from each of said plurality of different spatial offsets with a different depth or distribution of depths within the sample.

36. The apparatus of claim 35 wherein the processor is arranged to combine said Raman features from said different spatial offsets to determine a separate temperature for each of one or more depths or distributions of depth within the sample.

37. The apparatus of claim 35, wherein the entry and collection regions are spatially offset by an offset by a distance in the range from 1 mm to 50 mm.

38. The apparatus of claim 35,
wherein the apparatus is a non-invasive clinical thermometer;
wherein the sub-surface volume comprises a tissue of a human or animal subject; and
wherein the temperature is a sub-surface temperature of the tissue.

39. Apparatus for measuring temperature within a volume of a sample having a surface, comprising:
a light source for generating probe light;
delivery optics arranged to direct the probe light to an entry region on the surface;
collection optics arranged to collect said probe light from a collection region on the surface, following scattering within the volume of the sample, the collection region being spatially offset from the entry region;
a spectral analyser arranged to detect Raman spectral features in the collected probe light; and
a processor arranged to determine a temperature of the volume from the Raman spectral features;
wherein the sample comprises a fluid within a containing wall, the apparatus being arranged such that the entry and collection regions are provided on said containing wall, and the volume of the sample comprises a volume of the fluid, such that the determined temperature of the volume is a temperature of the fluid,
wherein the containing wall at least partly defines a conduit within which the fluid is flowing, or the containing wall is a wall of a bioreactor and the fluid comprises reagents within the bioreactor.

40. The apparatus of claim 39 further comprising said containing wall and said fluid, wherein said fluid is diffusely scattering.

41. The apparatus of claim 39, wherein the entry and collection regions are disposed on opposite sides of the sample.

42. The apparatus of claim 39 further comprising an offset driver arranged to provide a plurality of different spatial offsets between said entry and collection regions of the sample, the apparatus being arranged to separately detect said Raman spectral features for each different spatial offset, and to associate the Raman features from each of said plurality of different spatial offsets with a different depth or distribution of depths within the sample.

43. The apparatus of claim 42, wherein the processor is arranged to combine said Raman features from said different spatial offsets to determine a separate temperature for each of one or more depths or distributions of depth within the sample.

44. Apparatus for measuring temperature within a volume of a sample having a surface, comprising:
a light source for generating probe light;
delivery optics arranged to direct the probe light to an entry region on the surface;
collection optics arranged to collect said probe light from a collection region on the surface, following scattering within the sub-surface volume of the sample, the collection region being spatially offset from the entry region;
a spectral analyser arranged to detect Raman spectral features in the collected probe light;
a processor arranged to determine a temperature of the volume from the Raman spectral features; and
a conveyor arranged to translate a plurality of said samples past the delivery optics and collection optics, the apparatus being arranged to sequentially determine temperature of a sub-surface volume of each of the samples.

45. The apparatus of claim 44 further comprising said containing wall and said fluid, wherein said fluid is diffusely scattering.

46. The apparatus of claim 44, wherein the entry and collection regions are disposed on opposite sides of the sample.

47. The apparatus of claim 44 further comprising an offset driver arranged to provide a plurality of different spatial offsets between said entry and collection regions of each sample, the apparatus being arranged to separately detect said Raman spectral features for each different spatial offset, and to associate the Raman features from each of said plurality of different spatial offsets with a different depth or distribution of depths within each sample.

48. The apparatus of claim 47 wherein the processor is arranged to combine said Raman features from said plurality of different spatial offsets to determine a separate temperature for each of one or more depths or distributions of depth within each sample.

* * * * *